United States Patent
Joutel et al.

(10) Patent No.: US 10,407,500 B2
(45) Date of Patent: Sep. 10, 2019

(54) IMMUNOLOGICAL TREATMENT OF CEREBRAL AUTOSOMAL DOMINANT ARTERIOPATHY WITH SUBCORTICAL INFARCTS AND LEUKOENCEPHALOPATHY

(71) Applicants: INSERM, Paris (FR); UNIVERSITÉ PARIS DIDEROT—PARIS 7, Paris (FR)

(72) Inventors: Anne Joutel, Paris (FR); Søren Christensen, Jyllinge (DK); Thorleif Jan Pedersen, Brønshøj (DK)

(73) Assignees: INSERM (Institut National de la Santé et de la Recherche Médicale), Paris (FR); Université Paris Didrerot—Paris 7, Paris (FR)

( * ) Notice: Subject to any disclaimer, the term of this patent is extended or adjusted under 35 U.S.C. 154(b) by 72 days.

(21) Appl. No.: 15/514,173

(22) PCT Filed: Sep. 18, 2015

(86) PCT No.: PCT/EP2015/071311
§ 371 (c)(1),
(2) Date: Mar. 24, 2017

(87) PCT Pub. No.: WO2016/046053
PCT Pub. Date: Mar. 31, 2016

(65) Prior Publication Data
US 2017/0247450 A1   Aug. 31, 2017

(30) Foreign Application Priority Data
Sep. 25, 2014 (DK) .................................. 2014 00547

(51) Int. Cl.
| | |
|---|---|
| A61K 39/395 | (2006.01) |
| C07K 16/18 | (2006.01) |
| C07K 16/28 | (2006.01) |
| A61K 39/00 | (2006.01) |
| C07K 14/705 | (2006.01) |
| C07K 14/71 | (2006.01) |

(52) U.S. Cl.
CPC .......... *C07K 16/28* (2013.01); *A61K 39/0005* (2013.01); *A61K 39/3955* (2013.01); *A61K 2039/505* (2013.01); *A61K 2039/575* (2013.01); *C07K 16/2863* (2013.01); *C07K 2317/24* (2013.01); *C07K 2317/30* (2013.01); *C07K 2317/33* (2013.01); *C07K 2317/34* (2013.01); *C07K 2317/56* (2013.01); *C07K 2317/565* (2013.01); *C07K 2317/92* (2013.01); *C07K 2317/94* (2013.01)

(58) Field of Classification Search
CPC ................ C07K 16/28; C07K 2317/56; C07K 2317/565; C07K 14/71; C07K 14/705; C07K 16/2863; C07K 16/2866; C07K 2317/30; C07K 2317/515; A61K 2039/505; A61K 39/39558; A61K 39/3955; A61K 39/395
See application file for complete search history.

(56) References Cited

U.S. PATENT DOCUMENTS

| | | | | |
|---|---|---|---|---|
| 7,935,791 | B2 * | 5/2011 | Fung | .................... C07K 14/705 530/387.1 |
| 9,879,083 | B2 * | 1/2018 | Okamura | ................ C07K 16/28 |
| 2011/0318787 | A1 * | 12/2011 | Lesnik Oberstein | ........................ C07K 14/70567 435/91.3 |

FOREIGN PATENT DOCUMENTS

| | | |
|---|---|---|
| WO | 2008/051797 A2 | 5/2008 |
| WO | 2008/076960 A2 | 6/2008 |

OTHER PUBLICATIONS

Chabriat et al. CADASIL. Lancet Neurol 8: 643-653, 2009.*
Ghezali et al. Notch3ECD immunotherapy improves cerebrovascular responses in CADASIL mice. Ann Neurol 84: 246-259, 2018.*
Joutel, A. Pathogenesis of CADASIL. Bioessays 33: 73-80, 2010.*
Joutel et al. Cerebrovascular dysfunction and microcirculation rarefaction precede white matter lesions in a mouse genetic model of cerebral ischemic small vessel disease. J Clin Invest 120(2): 433-445, 2010.*
Lloyd et al. Protein Engineer Design and Selection 22(3): 159-168, 2009.*
Monet-Lepretre et al. Abnormal recruitment of extracellular matrix proteins by excess Notch3ECD: a new pathomechanism in CADASIL. Brain 136: 1830-1845, 2013.*
Zhang et al. Latent Notch3 epitopes unmasked in CADASIL and regulared by protein redox state. Brain Res 1583: 230-236, 2014.*
Joutel A et al: "The Ectodomain of the Notch3 Receptor Accumulates Whitin the Cerebrovasculature of CADASIL Patients", Journal of Clinical Investigation, American Society for Clinical Investigation, US, vol. 105, No. 5, Mar. 1, 2000, pp. 597-605.
Li Kang et al: "Modulation of Notch signaling by antibodies specific for the extracellular negative regulatory region of Notch3", Journal of Biological Chemistry, American Society for Biochemistry and Molecular Biology, US, vol. 283, No. 12, Mar. 21, 2008, pp. 8046-8054.

(Continued)

*Primary Examiner* — Bridget E Bunner
(74) *Attorney, Agent, or Firm* — W & C IP

(57) ABSTRACT

The present invention relates to an anti-Notch 3 antibody therapy useful for treatment of patients with cerebral autosomal dominant arteriopathy with subcortical infarcts and leukoencephalopathy. In particular, the invention relates to an anti-Notch3 antibody or a fragment thereof having a 2 fold, 4 fold or 10 fold higher affinity to Notch 3 than to Notch 1 or Notch 2 for use in therapy.

10 Claims, 8 Drawing Sheets

Specification includes a Sequence Listing.

(56) References Cited

OTHER PUBLICATIONS

Mohammad A. Y. Alqudah et al: "NOTCH3 Is a Prognostic Factor That Promotes Glioma Cell Proliferation, Migration and Invasion via Activation of CCND1 and EGFR", PLOS One, vol. 8, No. 10, Oct. 15, 2013, pp. e77299.

Marie Magdeleine Ruchoux et al: "Transgenic Mice Expressing Mutant Notch3 Develop Vascular Alterations Characteristic of Cerebral Autosomal Dominant Arteriopathy with Subcortical Infarcts and Leukoencephalopathy", Jan. 1, 2003.

* cited by examiner

A

B

D

E

IMMUNOLOGICAL TREATMENT OF CEREBRAL AUTOSOMAL DOMINANT ARTERIOPATHY WITH SUBCORTICAL INFARCTS AND LEUKOENCEPHALOPATHY

FIELD OF THE INVENTION

The present invention relates to an anti-Notch 3 antibody therapy useful for treatment of patients with cerebral autosomal dominant arteriopathy with subcortical infarcts and leukoencephalopathy.

BACKGROUND OF THE INVENTION

The Notch gene was first described in 1917 when a strain of the fruit fly *Drosophila melanogaster* was found to have notched wing blades (Morgan, Am Nat 51:513 (1917)). The gene was cloned some seventy years later and turned out to be a cell surface receptor playing a key role in the development of many different cell types and tissues (Wharton et al., Cell 43:567-581 (1985)). Since then, the gene and its molecular mechanisms have been extensively studied. The generality of the Notch pathway manifests itself at different levels.

The Notch signaling pathway was soon found to be an evolutionarily conserved signaling mechanism from *Drosophila* to vertebrates and has been found to be involved in many cellular processes, such as differentiation, cell fate decisions, maintenance of stem cells, proliferation, and apoptosis, in various cell types during and after development (See review Artavanis, et al., Science 268:225 (1995)). Knockout mutations were found to be lethal in embryonic mice (Krebs et al. Genes & Dev 14(11):1343-52 (2000). The expression of mutant forms of Notch in developing Xenopus embryos interfere profoundly with normal development (Coffman, et al., Cell 73 (1993)). In humans, there have been several genetic diseases linked to Notch mutations (Artavanis-Tsakonas, et al. Science 284:770-776 (1999)).

Mammals possess four Notch proteins (designated Notch 1 to 4) and five corresponding ligands (Delta-1, -3, and -4, and Jagged-1 and -2). The mammalian Notch gene encodes a ~300 kd protein that is cleaved during its transport to the cell surface and consequently exists as a heterodimer (NotchECD-NotchTMIC). The extracellular portion has many epidermal growth factor (EGF)-like repeats followed by three cysteine-rich Notch/Lin12 repeats (LN) (Wharton, et al, Cell 43:567 (1985); Kidd, et al, Mol Cell Biol 6:3431 (1986); Kopczynski, et al, Genes Dev 2:1723 (1988); Yochem, et al, Nature 335:547 (1988)). The amino-terminal EGF-like repeats participate in ligand binding, whereas the C-terminal part of the extracellular portion, including the Lin 12 repeats, prevent signaling in the absence of ligand. The signal induced by ligand binding is transmitted to the nucleus by a process involving proteolytic cleavage of the receptor and nuclear translocation of the intracellular domain (Notch-IC). After entering the nucleus, Notch-IC competes with inhibitory proteins and recruits coactivators, including mastermind-like (MAML) proteins, and acetyltransferases. The Notch-IC complex then binds to a transcription factor RBP-J to convert it from a transcriptional repressor to an activator. The few transcriptional factors identified so far vary in their nature and effects on the cell.

Cerebral autosomal dominant arteriopathy with subcortical infarcts and leukoencephalopathy (CADASIL) causes a type of stroke and dementia whose key features include recurrent subcortical ischaemic events and vascular dementia. Prominent manifestations on neuroimaging include extensive white matter lesions, lacunes and progressive brain atrophy. The disease is caused by highly stereotyped mutations that alter the number of cysteine residues in the extracellular domain of NOTCH3 (Joutel, A et al. 1997. The Lancet 350(9090):1511-5) which is predominantly expressed in vascular smooth muscle cells and pericytes of brain capillaries (Joutel, A et al. 2000. J Clin Invest 105 (5): 597-605). The two hallmark pathologies are extracellular NOTCH3 and GOM deposits, characteristically seen in close vicinity to the plasma membrane of vascular smooth muscle cells in the brain and peripheral vessels as well as of pericytes in the brain capillaries. NOTCH3 deposits are aggregates of the extracellular domain of NOTCH3 (Notch3ECD) and GOM are proteinaceous aggregates, with Notch3ECD being one important constituent (Joutel, A et al. 2000. J Clin Invest 105 (5): 597-605) (Ishiko et al. 2006 Acta Neurophatol 112(3):333-39) (Monet-Leprêtre et al. 2013. Brain: A journal of Neurology 136 (pt 6): 1830-45). Yet, today there are no therapies to prevent or halt the progression of the disease manifestations.

The inventors of the present invention have surprisingly found that anti-Notch 3 antibodies may be used in the treatment of CADASIL patients.

SUMMARY OF THE INVENTION

The invention relates to notch3 antibodies or fragments thereof. These antibodies are characterised by inter alia having a 2 fold, 4 fold or 10 fold higher affinity to Notch 3 than Notch 1 or Notch 2. In particular the antibodies are able to bind the Notch3ECD deposits, and an epitope comprised in amino acids 40-1643 of human Notch3 (SEQ ID NO: 3).

In a specific embodiment the CDR regions of the antibody comprises a heavy chain variable region H-CDR1 comprising SEQ ID NO: 8 a heavy chain variable region H-CDR2 comprising SEQ ID NO: 9 a heavy chain variable region H-CDR3 comprising SEQ ID NO: 10 a light chain variable region L-CDR1 comprising SEQ ID NO:12 a light chain variable region L-CDR2 comprising SEQ ID NO: 13 and a light chain variable region L-CDR3 comprising SEQ ID NO:14

The invention also relates to a vaccine comprising amino acids 40-1643 of human Notch3 (SEQ ID NO: 3) or a fragment thereof or amino acids 657-846 of human Notch3 (SEQ ID NO 7) or a fragment thereof. Such fragments comprise an epitope of Notch3.

Both the antibodies and the vaccines of the invention are useful in therapy and more particularly in treating CADASIL patients.

Two months old Tg PAC-Notch3R169C mice were treated for 4 months with weekly intraperitoneal injections of 10 mg/kg of 5E1 (6 mo-5E1, n=5 males) or control IgG1 (6 mo-IgG1, n=5 males) antibodies. A-B Representative electron micrographs of the middle cerebral artery of 6 month old Tg PAC-Notch3R169C mice treated with IgG1 (A) or 5E1 (B). GOM deposits are identified by red arrowheads. C— Diagram showing the number of GOM deposits in 6 month old treated Tg PAC-Notch3R169C mice showing that the 5E1 treatment does not prevent the appearance of GOM deposits. Scale bar is 5 μm. (Examples 10 and 11).

FIG. 4 shows that 5E1 chronic treatment protects from cerebrovascular dysfunction.

Two months old Tg PAC-Notch3R169C mice were treated for 4 months with weekly intraperitoneal injections of 10 mg/kg of 5E1 (TgN3R169C-5E1, n=5 males) or control IgG1 (TgN3R169C-IgG1, n=6 males) antibodies and analyzed at 6 months of age for cerebral blood flow (CBF) responses by laser Doppler flowmetry. An additional group of untreated wildtype mice (WT, n=5 males) aged 6 months was tested in parallel. 5E1 treatment significantly improves attenuation in the increased CBF produced by endothelium vasodilators Acetylcholine, Calcium ionophore A23187 and Bradykinin (A), smooth muscle relaxant adenosine (B) and neural activity (whisker stimulation) (C). (***$p<0.001$, TgN3R169C-5E1 compared to TgN3R169C-IgG1 or WT mice). Data are expressed as means±SEM and were analyzed by one-way ANOVA followed by Bonferroni post hoc test. (Examples 10 and 12).

Figures 4A, 4B, 4C:
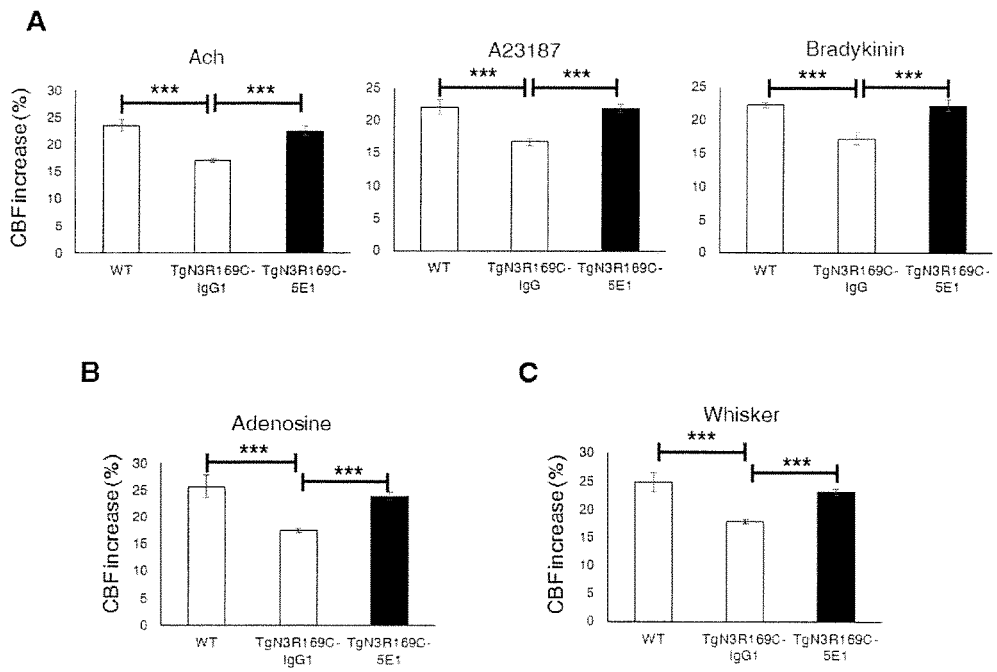
Figure 4D:
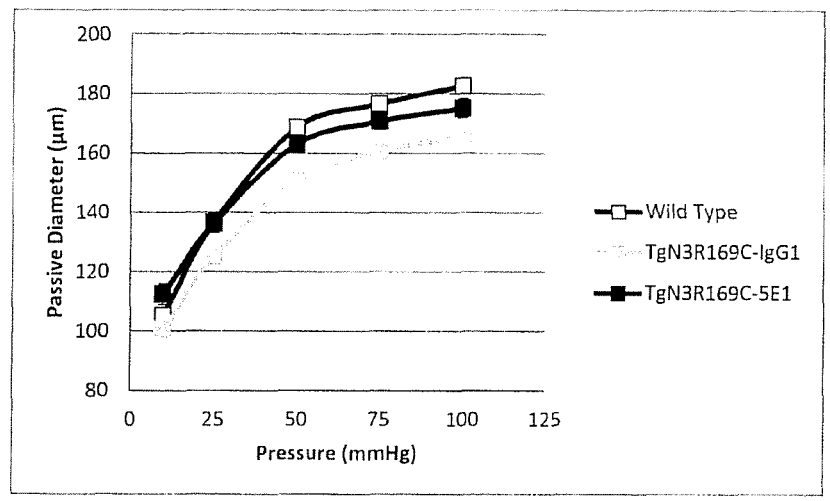
Figure 4E:
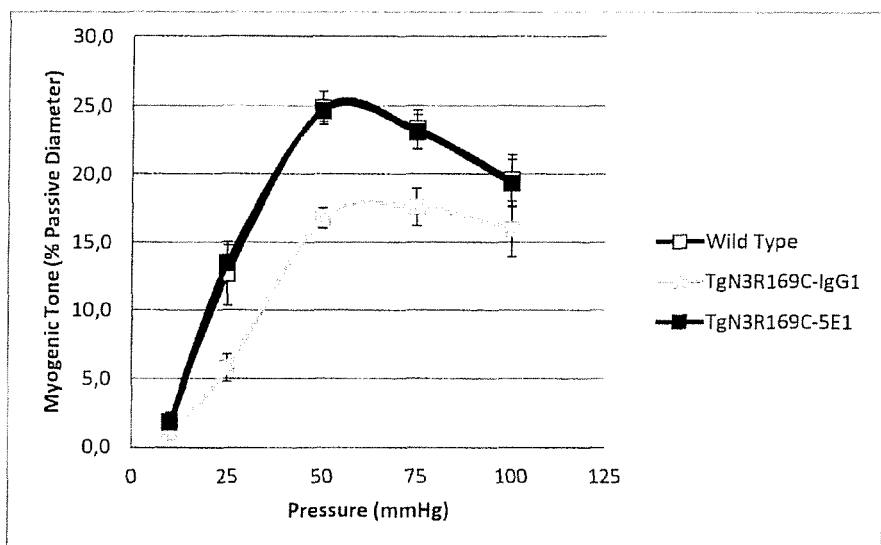

FIGS. 4D-4E shows that 5E1 chronic treatment protects against inward remodeling and reduced myogenic tone of brain arteries.

Two months old TgPAC-Notch3R169C mice were treated for 4 months with weekly intraperitoneal injections of 10 mg/kg of 5E1 (TgN3R169C-5E1, n=7 males) or control IgG1 (IgN3R169C-IgG1, n=7 males) antibodies and analyzed at 6 months of age for passive diameter (inward remodeling) and active diameter (myogenic tone) of pressurized posterior cerebral arteries using an arteriograph system. An additional group of untreated wild-type mice (WT, n=7 males) aged 6 months was tested in parallel. 5E1 treatment significantly improves reduction in the passive diameter (D) and normalizes the myogenic responses (E). (*$p<0.05$, ***$p<0.001$, TgN3R169C-5E1 compared to TgN3R169C-IgG1 mice). Data are expressed as means ±SEM and were analyzed by two-way repeated measures ANOVA followed by Bonferroni post hoc test. (Examples 10 and 13).

Figure 5:
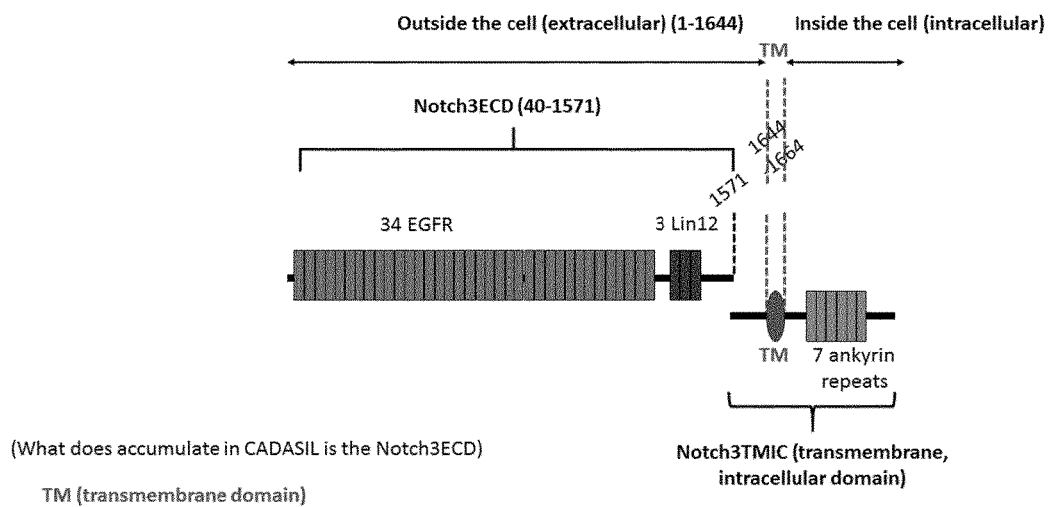

FIG. 5 shows a schematic presentation of human NOTCH3. Amino acids 1-39 constitute the signal peptide, amino acids 40-1643 constitute the extra cellular domain, amino acids 1644-1664 constitute the transmembrane domain, and amino acids 1665-2321 constitute the Notch 3 intracellular domain. Amino acids 1571-1572 is the cleavage site by furine like protease and amino acids 40-1571 constitutes the Notch3ECD (which abnormally accumulates in CADASIL).

Figure 6:
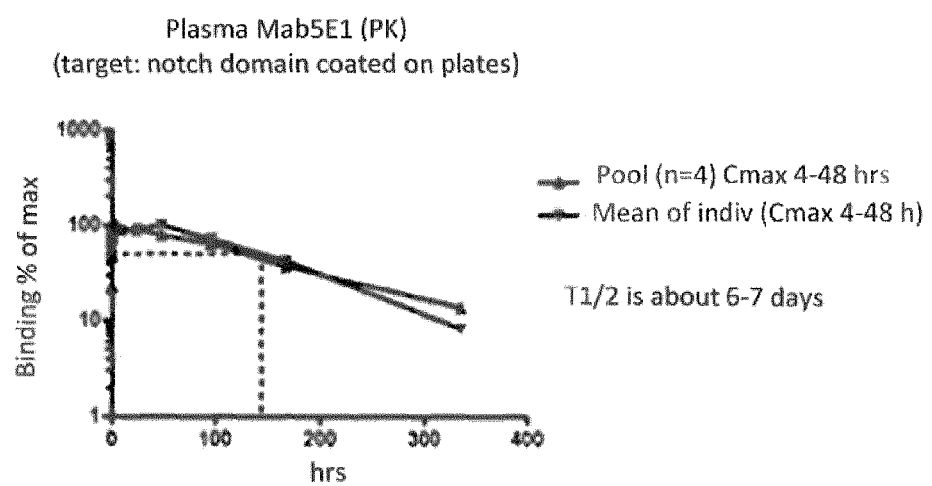

FIG. 6 shows determination of antibody plasma kinetics (Example 7). $T_{1/2}$ was determined to be 6-7 days and $C_{max}$ (4 hours) was about 500 ug/ml. Quantitation of free plasma mAb level was performed using 5E1 as standard and Notch domain coated plates.

DETAILED DESCRIPTION OF THE INVENTION

Definitions

The term "Notch3" is synonym to the Notch 3 polypeptide and refers to a polypeptide with the amino acids sequence given in SEQ ID NO: 1 (UniProt number Q9UM47), unless another meaning is clear from the context it is given. In SEQ ID NO: 1 amino acids 1-39 constitute the signal peptide (SEQ ID NO: 2), amino acids 40-1643 constitute the extra cellular domain (SEQ ID NO: 3), amino acids 1644-1664 constitute the transmembrane domain (SEQ ID NO: 4), and amino acids 1665-2321 constitute the Notch 3 intracellular domain (SEQ ID NO: 5). Amino acids 1571-1572 is the cleavage site by furine like protease and amino acids 40-1571 constitutes the Notch3ECD (SEQ ID NO: 6) (which abnormally accumulates in CADASIL).

The term "antibody" refers to an intact immunoglobulin or a functional fragment thereof. The term "isolated antibody" means throughout this specification an immunoglobulin antibody that exists in a physical milieu distinct from that in which it may occur in nature, and differs in chemical formula or sequence from a naturally-occurring protein. The term isolated antibody thus does not include non-isolated antibodies, such as polyclonal antibodies that are naturally occurring, but does include monoclonal antibodies (mAbs) as well as isolated antibody-like polypeptides, chimeric antibodies, humanized antibodies and fragments of isolated antibodies that possess the ability to bind an epitope.

Naturally occurring antibodies typically comprise a tetramer which is usually composed of at least two heavy (H) chains and at least two light (L) chains. Each heavy chain is comprised of a heavy chain variable region (abbreviated herein as VH) and a heavy chain constant region, usually comprised of three domains (CH1, CH2 ad CH3). Heavy chains can be of any isotype, including IgG (IgG1, IgG2, IgG3 and IgG4 subtypes), IgA (IgA1 and IgA2 subtypes), IgM and IgE. Each light chain is comprised of a light chain variable region (abbreviated herein as VL) and a light chain constant region (CL). Light chain includes kappa chains and lambda chains. The heavy and light chain variable region is typically responsible for antigen recognition, whilst the heavy and light chain constant region may mediate the binding of the immunoglobulin to host tissues or factors, including various cells of the immune system (e.g., effector cells) and the first component (Clq) of the classical complement system. The VH and VL regions can be further subdivided into regions of hypervariability, termed complementarity determining regions (CDR), interspersed with regions that are more conserved, termed framework regions (FR). Each VH and VL is composed of three CDRs and four FRs arranged from amino-terminus to carboxy-terminus in the following order: FR1, CDR1, FR2, CDR2, FR3, CDR3, FR4. The variable regions of the heavy and light chains The terms "monoclonal antibody" or "mAb" as used herein refer to a preparation of isolated antibody molecules of single molecular composition. A monoclonal antibody composition displays a single binding specificity and affinity for a particular epitope. Accordingly, the term "human monoclonal antibody" refers to antibodies displaying a single binding specificity which have variable and constant regions derived from human germline immunoglobulin sequences. The human monoclonal antibodies may be produced by a hybridoma which includes a B cell obtained from a transgenic or transchromosomal non-human animal, such as a transgenic mouse, having a genome comprising a human heavy chain transgene and a light chain transgene, fused to an immortalized cell.

As used herein, "isotype" refers to the immunoglobulin class (for instance IgG1, IgG2, IgG3, IgG4, IgD, IgA, IgE, or IgM) that is encoded by heavy chain constant region genes.

The term "humanized antibody" as used herein, is intended to include isolated antibodies having variable and constant regions derived from human germline immunoglobulin sequences. The antibody or fragment thereof may be fully or partially humanized by methods known by the skilled artesian whereby, for example, the CDR sequences derived from the germline of another mammalian species, such as a mouse, have been grafted onto human framework sequences.

As indicated herein-above, the term antibody herein may include fragments of an antibody that retain the ability to specifically bind to the antigen. It has been shown that the antigen-binding function of an antibody may be performed by fragments of a full-length antibody, e.g., Fab and F(ab')$_2$ fragments.

Antibody fragments can be obtained by conventional techniques, such as by fragmentation of full-length antibodies or by expression of nucleic acids encoding antibody fragments in recombinant cells (see, for instance Evans et al., J. Immunol. Meth. 184, 123-38 (1995)). The fragments can then be tested or screened for their properties in the same manner as described herein for full-length antibodies. Examples of antibody fragments includes for examples the below:

F(ab')$_2$ fragments, which are bivalent fragments comprising two Fab fragments linked by a disulfide bridge at the hinge region. These can be generated by, e.g., treating a full-length antibody with pepsin.

Fab' or Fab fragments, which are monovalent fragments consisting of the $V_L$, $V_H$, $C_L$ and $C_H 1$ domains. Fab fragments can be obtained, e.g., by treating an IgG antibody with papain. Fab' fragments can be obtained, e.g., by reducing the disulfide bridges of a F(ab')$_2$ fragment using a reducing agent such as dithiothreitol.

Fv fragments, which consist essentially of the $V_L$ and $V_H$ domains of a single arm of an antibody and single-chain antibodies thereof. Single-chain antibodies (also known as single chain Fv (scFv) antibodies) are constructs where the $V_L$ and $V_H$ domains of an Fv fragment are joined, using recombinant methods, by a synthetic linker that enables them to be expressed as a single protein chain in which the $V_L$ and $V_H$ regions pair to form monovalent molecules (see for instance Bird et al., Science 242, 423-426 (1988) and Huston et al., PNAS USA 85, 5879-5883 (1988)).

Domain antibodies (also called dAb fragments), which consists essentially of a $V_H$ domain (see, e.g., Ward et al., Nature 341, 544-546 (1989); Holt et al; Trends Biotechnol. 2003 November; 21(11):484-90).

Other exemplary formats include camelids or nanobodies (see, e.g., Revets et al; Expert Opin Biol Ther. 2005 January; 5(1):111-24

The term "epitope" means a portion of an antigen (e.g., a protein determinant of an antigen) that is capable of specific binding by an antibody. The epitope may comprise amino acid residues which are directly involved in the binding, and other amino acid residues, which are not directly involved in the binding, such as amino acid residues which are effectively blocked or covered by the specific antigen binding peptide (in other words, the amino acid residue is within the footprint of the specific antigen binding peptide).

As used herein, the term "binding" in the context of the binding of an antibody to a predetermined antigen or epitope typically is a binding with an affinity corresponding to a $K_D$ of about $10^{-7}$ M or less, such as about $10^{-8}$ M or less, such as about $10^{-9}$ M or less, about $10^{-19}$ M or less, or about $10^{-11}$ M or even less when determined by for instance surface plasmon resonance (SPR) technology in a BIAcore 3000 instrument using a soluble form of the antigen as the ligand and the antibody as the analyte. Typically, an antibody binds to the predetermined antigen with an affinity corresponding to a $K_D$ that is at least ten-fold lower, such as at least 100-fold lower, for instance at least 1,000-fold lower, such as at least 10,000-fold lower, for instance at least 100,000-fold lower than its $K_D$ for binding to a non-specific antigen (e.g., BSA, casein), which is not identical or closely related to the predetermined antigen. When the $K_D$ of the antibody is very low (that is, the antibody has a high affinity), then the $K_D$ with which it binds the antigen is typically at least 10,000-fold lower than its $K_D$ for a non-specific antigen. An antibody is said to essentially not bind an antigen or epitope if such binding is either not detectable (using, for example, plasmon resonance (SPR) technology in a BIAcore 3000 instrument using a soluble form of the antigen as the ligand and the antibody as the analyte), or is 100 fold, 500 fold, 1000 fold or more than 1000 fold less than the binding detected by that antibody and an antigen or epitope having a different chemical structure or amino acid sequence.

The term "$k_d$" (sec$^{-1}$), as used herein, refers to the dissociation rate constant of a particular Ab-antigen interaction ([Ab][antigen]/[Ab-antigen complex]). Said value is also referred to as the $k_{off}$ value.

The term "$k_a$" (M$^{-1}\times$sec$^{-1}$), as used herein, refers to the association rate constant of a particular Ab-antigen interaction and is the reciprocal of the $k_d$.

The term "$K_D$" (M), as used herein, refers to the dissociation equilibrium constant of a particular Ab-antigen interaction and is obtained by dividing the $k_d$ by the $k_a$.

The term "$K_A$" ($M^{-1}$), as used herein, refers to the association equilibrium constant of a particular Ab-antigen interaction and is obtained by dividing the $k_a$ by the $k_d$.

Specific Embodiments and Aspects of the Invention

Figure 1:
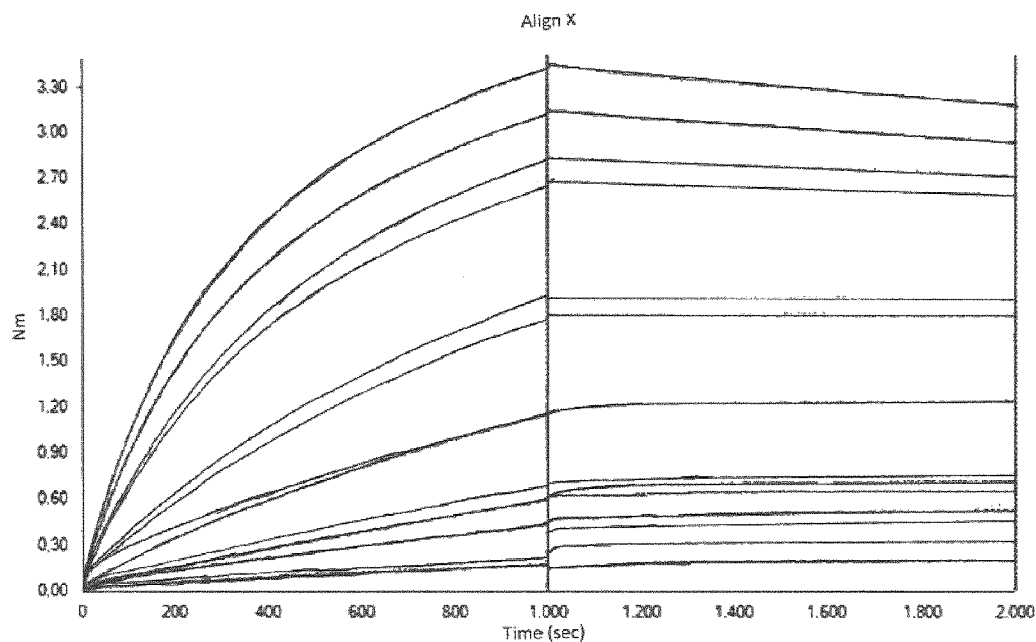
FIG. 1 shows 5E1 binding to human NOTCH3 using OCTET analysis. (A) Kinetic analysis was performed using the Octet RED technology from ForteBio according to the manufactures instruction. Biotinylated NOTCH3 657-848 was immobilized on streptavidin tips at a level of approximately 3 RU each. (B) Subsequent association and dissociation of 5E1 antibody was analyzed at concentrations in the range from 333 nM to 3.3 nM. Data analysis was subsequently done using the ForteBio Data Analysis 7.0 software (Example 3).
Figure 1:
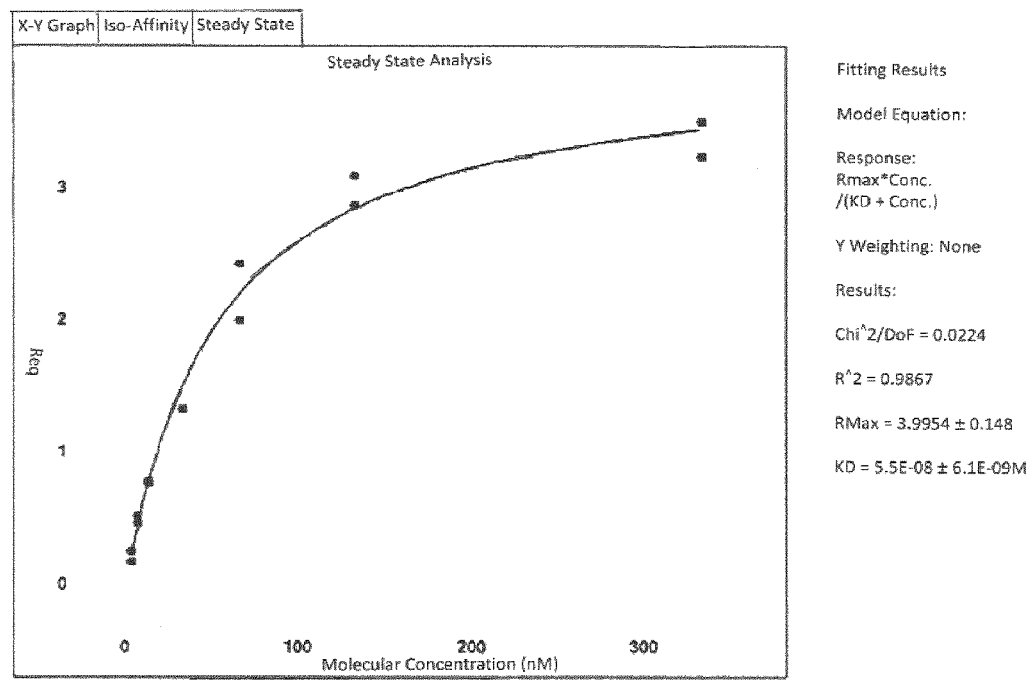

The present invention relates to anti-Notch3 antibody therapy of CADASIL patients as exemplified by the isolated antibody 5E1 (Examples 1 and 2), which is a murine monoclonal antibody that binds to human Notch3 but neither to Notch1 nor Notch2. The isolated 5E1 antibody additionally has the ability to i.a. detect vascular NOTCH3ECD deposits in both human, mouse and rats, and thereby provide an antibody with exceptional good translation into human pathology from animal models. The 5E1 antibody was raised against human Notch3 and recognizes both human and rat NOTCH3 with close binding constants (KD=55 nM) (FIG. 1, Example 3).

Figures 2A, 2O:
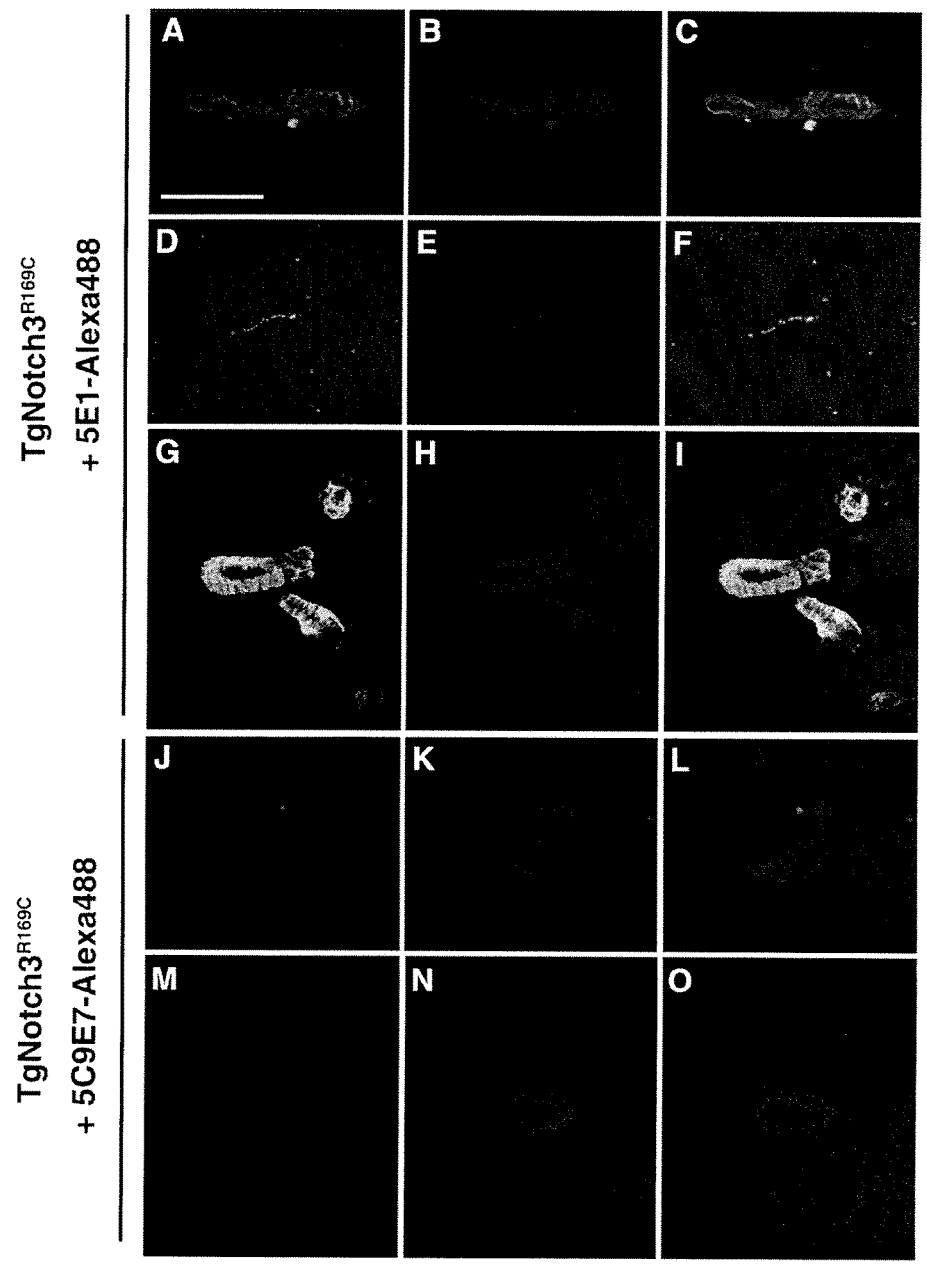
FIG. 2 shows 5E1 enters the CNS and binds to vascular Notch3ECD deposits in old mice. Old Tg PAC-Notch3R169C mice (10-12 months old) received a single 10 mg/kg intraperitoneal injection of Alexa 488-conjugated 5E1 (A-I) or 5C9E7 control antibody (J-O) (Example 8). The antibody in vivo binding to Notch3ECD deposits was assessed 3 days after injection on cryosections of brain (A-F; J-L) and kidney (G-I; M-O) immunolabeled with exogenous anti-Notch3ECD-antibody and detected with Alexa 594 secondary antibodies. Shown is the fluorescence emission by the Alexa 488 (injected antibody) (left column), the Alexa 594 (exogenous antibody) (middle column) and the merged images (right column). 5E1 binds to Notch3ECD deposits in brain arteries (A-C), brain capillaries (D-F) and kidney arteries (G-I). Although images displayed on G and M have been acquired using a four times shorter exposure, the kidney artery displays a brighter signal than the brain vessels. (scale bar represents 95 μm except in panels D-F where it represents 60 μm).
FIGS. 2P-2R shows 5E1 enters the CNS and binds to vascular Notch3ECD deposits in young mice. Young Tg PAC-Notch3R169C mice (2 months old) received a single 10 mg/Kg intraperitoneal injection of unconjugated 5E1 antibody (Example 9). The antibody in vivo target engagement was assessed 3 days after injection on brain sections coimmunolabeled with Alexa 594 conjugated antibody against mouse immunoglobulin (P, detection of 5E1 binding), and Alexa488 conjugated 5E1 (Q, detection of total Notch3ECD deposits). The merged image (R) indicates that the target engagement is almost complete. (scale bar represents 76 μm). (Example 9).

Peripherally administered anti-Notch3 antibodies acts directly on vascular Notch3ECD deposits and crosses the blood brain barrier prior to reaching the deposits, as shown for 5E1 (FIG. 2, Example 8). In an experiment in old TgPAC-Notch3R169C mice displaying abundant Notch3ECD deposits in both the brain vessels and peripheral arteries, ten to twelve months old TgPAC-Notch3R169C and control mice received a single injection of Alexa 488-conjugated anti-Notch3 antibody (5E1) or 5C9E7 control antibody (10 mg/kg). Mice were subsequently sacrificed 3 days later and cryostat sections of the brain and kidney were examined by direct fluorescence. Brain vessels (including arteries and capillaries) of the anti-Notch3 antibody treated TgPAC-Notch3R169C mice were labelled whereas vessels of the 5C9E7-treated group were unstained (FIG. 2 A, D and J). Notably, in the anti-Notch3 antibody treated TgPAC-Notch3R169C mice, peripheral arteries were far more strongly stained than the brain vessels (FIG. 2, G compared to A and D). Co-immunolabelling of the sections with an anti-Notch3ECD antibody indicated that the 5E1 antibody had bound almost all Notch3ECD deposits in mutant mice in both the brain and kidney vessels (FIG. 2 B,C, E,F, H,I). Thus the data indicated that anti-Notch3 antibodies can bind to vascular Notch3ECD deposits in vivo and that a small fraction can enter the brain to act directly on Notch3ECD deposits in the brain vasculature.

Figures 2P, 2Q, 2R:
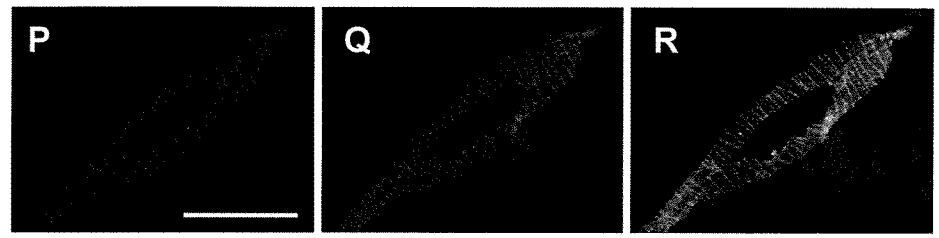

Old TgPAC-Notch3R169C mice might exhibit subtle blood brain barrier defects. This may favour the diffusion of antibodies into the brain. To investigate this the inventors of the present invention conducted experiments in younger TgPAC-Notch3R169C mice (Example 9). Two months old TgPAC-Notch3R169C mice received a single intraperitoneal injection of unconjugated an anti-Notch3 antibody (5E1) or control IgG1 (10 mg/kg) and were subsequently sacrificed 3 days later to study the target engagement. Immunofluorescence analysis of brain cryosections with an anti-mouse antibody revealed that the anti-Notch3 antibody robustly engaged Notch3ECD aggregates in the brain vessels (FIG. 2P). Moreover, coimmunolabeling with Alexa 488-conjugated anti-Notch3 antibody (5E1) was done to determine the total amount of Notch3ECD deposits and indicated that the percentage of target engagement was close to 100% (FIG. 2Q and 2R). Hence, it can be concluded that anti-Notch 3antibodies are suitable for a vaccinotherapy approach.

The observation that anti-Notch 3 antibodies binds to Notch3ECD deposits indicates a promising therapeutic application in CADASIL patients because it could also be efficacious at preventing or lowering vascular Notch3ECD or GOM deposits.

Figure 3:
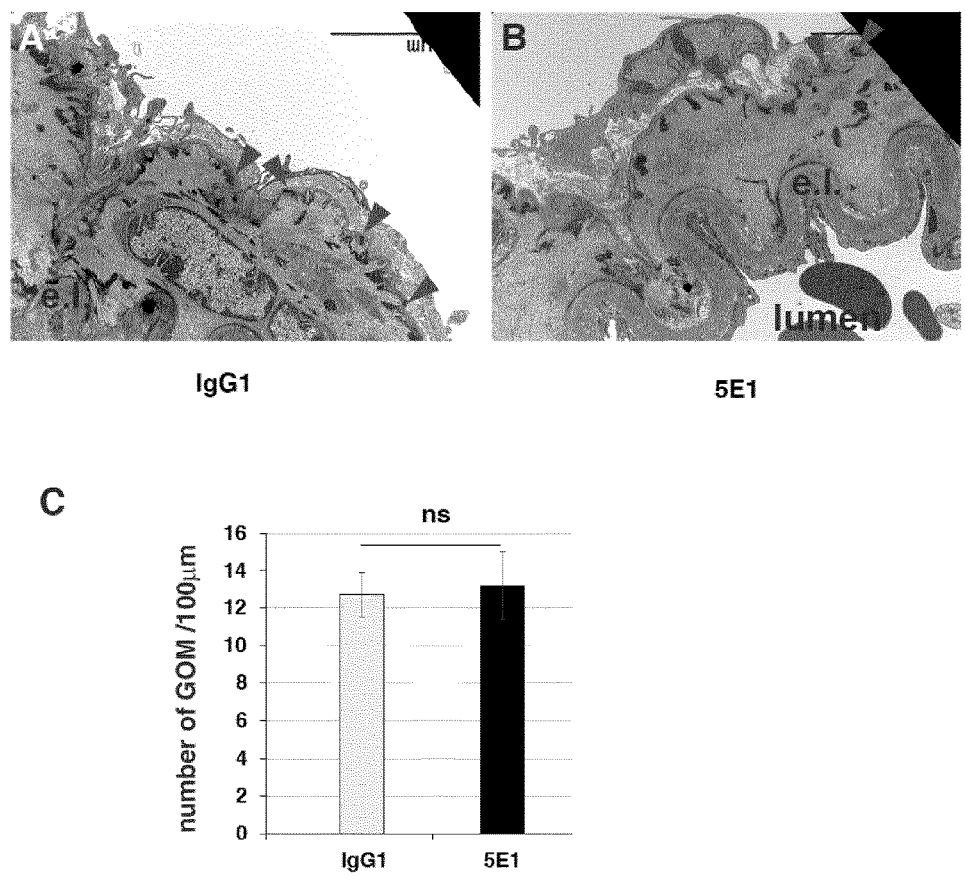
FIG. 3 shows 5E1 treatment does not prevent GOM deposits.

Brain vessels consist of a network of small arteries which travel on the brain surface (pial arteries), branch extensively into smaller arteries that penetrate into the brain parenchyma (penetrating arteries) and then terminate as an extensive capillary network (capillaries). In TgPAC-Notch3R169C mice, Notch3ECD aggregates are detectable in the pial arteries from birth, then aggregates extend gradually to the small penetrating arteries and the capillaries between 2 and 6 months of age. GOM deposits, which are scattered at 1 month, become readily detectable by 6 months of age in the pial arteries (Joutel A, Monet-Leprêtre M, Gosele C, Baron-Menguy C, Hammes A, Schmidt S, Lemaire-Carrette B, Domenga V, Schedl A, Lacombe P, Hubner N. 2010. "Cerebrovascular dysfunction and microcirculation rarefaction precede white matter lesions in a mouse genetic model of cerebral ischemic small vessel disease." J Clin Invest 120 (2):433-45). Therefore, the inventors initiated a study, in which TgPAC-Notch3R169C mice were treated from 2 to 6 months (Example 10), in order to explore the attenuation of preexisting NOTCH3 deposits in pial arteries and prevention of new NOTCH3ECD deposits in the intraparenchymal vessels as well as prevention of GOM deposits. On the basis of the results of the pharmacokinetics study showing that anti-Notch3 antibodies (as exemplified with 5E1) had a plasma half-life of 6-7 days (FIG. 6 and Example 7), mice were treated with weekly injections of anti-Notch3 antibodies (5E1) or control IgG1 at 10 mg/kg. A group of TgPAC-Notch3R169C mice were sacrificed at 2 months of age (time zero) to determine the extent of existing NOTCH3ECD and GOM deposits prior to treatment. Brain sections were processed for quantitative immunohistochemical analyses of Notch3ECD aggregates, using an exogenous polyclonal antibody against the N-ter of NOTCH3, a domain which is not recognized by 5E1, or using a polyclonal antibody against the EGFR17-21 of rat NOTCH3 (Example 11). A comparison of the time zero (2 months) versus the control IgG1 (6 months) animals showed an age-dependent accumulation of Notch3ECD aggregates that increase in the pial and capillaries. Brain tissue was also processed for quantitative electron microscopy analyses of GOM deposits on ultrathin sections of the middle cerebral artery (Example 11). Importantly, quantification of GOM deposits revealed no significant difference between the anti-Notch3 antibodies and control antibodies treated mice (n=5 males per group) (FIG. 3).

It was however observed that anti-Notch3 antibody treatment protects against in vivo cerebrovascular dysfunction, and thus provide a beneficial treatment option for CADASIL patients.

Using an open cranial window on the somatosensory cortex of anesthetized mice and laser Doppler flowmetry to measure cerebral blood flow (CBF), the CBF increase evoked by neocortical application of both the endothelium-dependent vasodilators Ach, bradykinin and the Ca2+ ionophore A23187, as well as responses to the smooth muscle relaxant adenosine were strongly reduced in TgPAC-Notch3R169C mice aged 6 months compared to both aged matched TgPAC-Notch3WT mice, which overexpress a similar amount of wiltype Notch3, and non-transgenic littermates suggesting that smooth muscle reactivity was impaired in mutant mice (Example 10 and 12). It was also found that CBF increase produced by facial whiskers stimulation (functional hyperemia) was strongly attenuated in TgPAC-Notch3R169C mice at 6 months of age compared to control mice (Joutel A, Monet-Leprêtre M, Gosele C, Baron-Menguy C, Hammes A, Schmidt S, Lemaire-Carrette B, Domenga V, Schedl A, Lacombe P, Hubner N. 2010. "Cerebrovascular dysfunction and microcirculation rarefaction precede white matter lesions in a mouse genetic model of cerebral ischemic small vessel disease." J Clin Invest 120 (2):433-45). Accordingly, this paradigm was a promising a mean to investigate whether or not anti-Notch3 antibody treatment could rescue the cerebrovascular dysfunction despite the lack of any detectable change in the load of Notch3ECD deposits.

First a parallel cohort of mutant and wildtype untreated mice at two months of age, ie time zero was assessed. It was found that at 2 months of age, functional hyperemia as well as the responses to both endothelium-dependent vasodilators and the smooth muscle vasorelaxant did not differ between TgPAC-Notch3R169C and the wildtype littermates (n=5 mice per group) Next TgPAC-Notch3R169C mice treated with weekly injections of anti-Notch3 antibodies (5E1) or control IgG1 at 10 mg/kg from 2 months to 6 months of age was examined. Anti-Notch3 antibody treated TgPAC-Notch3R169C mice had significantly improved CBF responses evoked by topical neocortical application of endothelium-dependent vasodilators (FIG. 4A) or smooth muscle relaxant adenosine (FIG. 4B) that were not significantly different from untreated 6 mo WT mice but that were significantly different from IgG1-treated TgPAC-Notch3R169C mice. Moreover, functional hyperemia in anti-Notch3 antibody treated TgPAC-Notch3R169C mice was also markedly improved (n=5-6 males per group) (FIG. 4C). Therefore, these data shows that passive immunization with an anti-Notch3 antibody, such as 5E1, can restore CBF responses in TgPAC-Notch3R169C mice to wild-type levels.

Using an arteriograph system to measure active and passive diameter of pressurized posterior cerebral arteries, we previously reported that pressure-induced constriction (myogenic tone) of brain arteries was markedly attenuated in TgPAC-Notch3R169C mice aged 6 months compared to both aged matched wildtype and TgPAC-Notch3WT mice. It was also found that the passive diameter of posterior cerebral arteries was markedly reduced in TgPAC-Notch3R169C mice aged 6 months compared to control mice whereas the wall thickness was unchanged indicative of an inward remodeling in these mice (Joutel A, Monet-Leprêtre M, Gosele C, Baron-Menguy C, Hammes A, Schmidt S, Lemaire-Carrette B, Domenga V, Schedl A, Lacombe P, Hubner N. 2010. "Cerebrovascular dysfunction and microcirculation rarefaction precede white matter lesions in a mouse genetic model of cerebral ischemic small vessel disease." J Clin Invest 120(2):433-45). Accordingly, this paradigm was a promising mean to investigate whether or not anti-Notch3 antibody treatment acts at the level of brain arteries to rescue the altered myogenic tone and the inward remodeling.

TgPAC-Notch3R169C mice treated with weekly injections of anti-Notch3 antibodies (5E1) or control IgG1 at 10 mg/kg from 2 months to 6 months of age were examined. An additional group of untreated wild-type mice aged 6 months was tested in parallel. Anti-Notch3 antibody treated TgPAC-Notch3R169C mice had significantly improved passive diameters that were not significantly different from untreated 6 mo WT mice but that were significantly different from IgG1-treated TgPAC-Notch3R169C mice (FIG. 4D). Moreover, anti-Notch3 antibody treated TgPAC-Notch3R169C mice had normalized myogenic responses that were comparable to untreated 6 mo WT mice (FIG. 4E). Therefore, these data show that passive immunization with an anti-Notch3 antibody, such as 5E1, acts at the level of brain arteries to protect against inward remodeling and reduced myogenic tone.

Thus, without being bound to an underlying hypothesis the inventors of the present invention have shown that anti-Notch3 antibodies binding to the ectodomain domain of Notch3 (Notch3ECD) provide a disease modifying therapy that may help patients suffering from CADASIL.

As outlined in the background section, Notch 3 belongs to a larger receptor family that also includes Notch 1, Notch 2 and Notch 4.

By overexpressing Notch 1, Notch 2, Notch 3 and Notch 4 different biological responses has been observed. These effects include cell proliferation, apoptosis, and inflammatory and profibrotic responses, depending on the particular Notch receptor. For example Notch 1, Notch 2 and Notch 4 have been observed in glomerular and tubular cells in human and experimental kidney disease (Shanzes-Nino et al., J Pathol 2012:228:266-273). To avoid any side effects with a therapeutic antibody, such as 5E1, it desirable to have as a specific antibody to its target as possible.

To avoid these side effects, the invention therefore relates to an anti-Notch 3 antibody or a fragment thereof that essentially does not bind to Notch 1 or Notch 2, and more preferably that also essentially does not bind to other related Notch receptors such as Notch 4 (Example 2). Antibody 5E1 is illustrative of the invention in having these properties and is very specific for Notch 3. 5E1 binds neither to human Notch1 nor human Notch2 (Joutel, A et al. 2000. J Clin Invest 105 (5): 597-605).

In one embodiment the invention relates to a therapeutic Notch3 antibody or a fragment thereof having a 2 fold, 4 fold or 10 fold higher affinity to Notch 3 than Notch 1 or Notch 2. In another embodiment the Notch 3 antibody or fragment essentially does not bind Notch 1 or 2. In yet a further embodiment the Notch 3 antibody or fragment essentially does not bind Notch 1, 2 or 4.

Binding can be determined by for example surface plasmon resonance (SPR) technology in a BIAcore 3000 instrument using a soluble form of the antigen as the ligand and the antibody as the analyte.

In one embodiment the Notch 3 antibody or fragment is binding to an epitope comprising amino acids 40-1643 (SEQ ID NO 3) of human Notch3, such as an epitope comprised in amino acids 657-846 (SEQ ID NO 7) of human Notch3.

The invention relates to an antibody or fragment thereof for use in therapy. Thus, the invention relates to i.a. a method for treating a patient suffering from CADASIL, or at risk thereof, wherein an antibody that binds to Notch3ECD is administered to such patient in an amount effective to treat such condition or risk, or wherein a fragment of Notch3 is administered to such patient in and amount and formulation sufficient to comprise a vaccine that elicits the production of antibodies that bind to Notch3ECD. Such a fragment may be or comprise a fragment of amino acids 40-1643 (SEQ ID NO 3), such as a fragment that is or comprises amino acids 657-846 (SEQ ID NO 7) of human Notch3.

In particular, the invention relates to an antibody or fragment thereof for use in therapy, wherein the antibody or fragment comprises:

a heavy chain variable region H-CDR1 comprising SEQ ID NO: 8 a heavy chain variable region H-CDR2 comprising SEQ ID NO: 9 a heavy chain variable region H-CDR3 comprising SEQ ID NO: 10 a light chain variable region L-CDR1 comprising SEQ ID NO: 12 a light chain variable region L-CDR2 comprising SEQ ID NO: 13 and a light chain variable region L-CDR3 comprising SEQ ID NO: 14

In another embodiment the antibody or fragment thereof comprises a heavy chain variable region comprising SEQ ID NO: 11 and/or comprises a light chain variable domain comprising SEQ ID NO: 15

The antibody or fragment thereof may be fully or partially humanized by methods known by the skilled artesian whereby, for example, the CDR sequences derived from the germline of another mammalian species, such as a mouse, have been grafted onto human framework sequences.

The antibody or fragment thereof are useful in therapy and in particular in CADASIL patients.

It's also envisaged that amino acids 40-1643 (SEQ ID NO 3) of human Notch3, such as an amino acids 657-846 (SEQ ID NO 7) of human Notch3, may be used in an active vaccine strategy in therapy and to treat CADASIL. Fragments in the size of e.g. 4, amino acids, 5 amino acids, 7 amino acids 10 amino acids or larger or for example in a range of 5-10, 5-15, or 5-20 amino acids of said sequences 40-1643 or 657-846 of human Notch3 may be used to vaccinate patients alone or in combination with an appropriate adjuvant such as e.g. such as aluminum hydroxide or phosphate.

Suitable dosage ranges are of the order of several hundred micrograms active ingredient per vaccination with a preferred range from about 0.1 pg to 2,000 ug (even though higher amounts in the 1-10 mg range are contemplated), such as in the range from about 0.5 ug to 1,000 ug, preferably in the range from 1 ug to 500 ug and especially in the range from about 10 ug to 100 ug. Suitable regimens for initial administration and booster shots are also variable but are typified by an initial administration followed by subsequent inoculations or other administrations.

The manner of application may be varied widely. Any of the conventional methods for administration of a vaccine are applicable. These include oral application on a solid physiologically acceptable base or in a physiologically acceptable dispersion, parenterally, by injection or the like. The dosage of the vaccine will depend on the route of administration and will vary according to the age of the person to be vaccinated and the formulation of the antigen.

It also envisaged that the treatment may also comprise a step of diagnosing the progress of the disease therapy by measuring the amount of deposits using an anti-Notch 3 antibody labelled by an appropriate label. The choice of label depends on the means of detection. For example, a fluorescent label, such as a rare earth chelate (e.g., a europium chelate), a fluorescein type label (e.g., fluorescein, fluorescein isothiocyanate, 5-carboxyfluorescein, 6-carboxy fluorescein, dichlorotriazinylamine fluorescein), a rhodamine type label (e.g., TAMRA or dansyl chloride), phycoerythrin; umbelliferone, Lissamine; cyanines; phycoerythrins, Texas Red, BODIPY-FL-SE, or an analog thereof, is suitable for optical detection. Chemoluminescent labels may be employed (e.g., luminol, luciferase, luciferin, and aequorin). Paramagnetic labels and radioactive labels can also be employed, and are preferably detected using PET or SPECT. Such radioactive materials include, but are not limited to, bismuth ($^{213}$Bi), carbon ($^{14}$C), chromium ($^{51}$Cr), cobalt ($^{57}$Co), fluorine ($^{18}$F), gadolinium ($^{153}$Gd, $^{159}$Gd), gallium ($^{68}$Ga, $^{67}$Ga), germanium ($^{68}$Ge), holmium ($^{166}$Ho), indium ($^{115}$In, $^{113}$In, $^{112}$In, $^{111}$In) iodine ($^{131}$I, $^{125}$I, $^{123}$I, $^{121}$I), lanthanium ($^{140}$La), lutetium ($^{177}$Lu), manganese ($^{54}$Mn), molybdenum ($^{99}$Mo), palladium ($^{103}$Pd), phosphorous ($^{32}$P), praseodymium ($^{142}$Pr), promethium ($^{149}$Pm), rhenium ($^{186}$Re, $^{188}$Re), rhodium ($^{105}$Rh), ruthemium ($^{97}$Ru), samarium ($^{153}$Sm), scandium ($^{47}$Sc), selenium ($^{75}$Se), strontium ($^{85}$Sr), sulfur ($^{35}$S), technetium ($^{99}$Tc), thallium ($^{201}$Ti), tin ($^{113}$Sn, $^{117}$Sn), tritium ($^{3}$H), xenon ($^{133}$Xe), ytterbium ($^{169}$Yb, $^{175}$Yb), yttrium ($^{90}$Y), zinc ($^{65}$Zn); positron emitting metals using various positron emission tomographies, and nonradioactive paramagnetic metal ions.

EXAMPLE 1

Generation of Hybridoma Clone 5E1

Human Notch3 cDNA coding for the extracellular epitope (amino acids 657-846) of the human Notch3 protein with a C-terminal stretch of 6 Histidine residues was inserted into the pACGP67B Baculovirus complementing transfer vector (Pharmingen) to be expressed as a gp67 signal peptide fusion protein under the control of the strong Baculovirus polyhedrin promoter. Sf9 cells grown as a mono layer were transfected with the transfer plasmid together with the modified baculovirus DNA (BaculoGold™ DNA, Pharmingen), which contains a lethal deletion, using the Insectin-Plus™ reagent (Invitrogen). Recombinant baculoviruses were identified and purified by virus plaque assay and the presence of Notch3 cDNA was confirmed by Southern blot. Recombinant baculoviruses carrying the Notch3 cDNA were then amplified to obtain a high titer solution ($10^8$-$10^9$ viral particles/ml). To produce the recombinant protein, 5. $10^7$ Sf9 cells, grown in T175 culture flasks as a mono layer in Grace's medium with fetal calf serum (20 ml) (Biowhittaker, Boehringer), were infected with 1.5 ml of high titer stock and incubated 3 to 4 days at 27° C. The supernatant, containing the recombinant protein, was then harvested, concentrated by ammonium sulfate (60%) precipitation. The pellet was resuspended in 300 mM NaCl50 mM NaH$_2$PO$_4$ pH 8.0 and dialyzed overnight against the same buffer. The dialyzed supernatant was purified over Ni2+ agarose beads and the recombinant protein was eluted in dialysis buffer containing 250 mM Imidazole. Purity of the protein was checked by SDS-PAGE analysis and coomassie blue staining.

Hybridomas were obtained by fusing myeloma cells with the spleen cells from mice immunized with the recombinant protein. Hybridomas culture supernatant were screened by immuno fluorescence and immunoblot, as described below in Example 2, to identify and select only those hybridomas producing antibodies that recognize Notch3 protein products but neither Notch1 nor Notch2 protein products. Positive hybridomas were further cloned generating several clones including one called "5E1".

EXAMPLE 2

Screening Assay for 5E1

293T cells were grown in Nunc® Lab-Tek® II chambered coverglass, 8 wells, and were transiently transfected by calcium phosphate precipitation with plasmids encoding for human full length Notch1, Notch2 or Notch3 cDNA or empty vector plasmids. Two days after transfection, cells were fixed in ethanol and processed for immunofluorescence using 5E1 anti-Notch3, anti-human Notch1, anti-human Notch2 primary monoclonal antibodies and appropriate FITC-conjugated antibodies. 5E1 antibody stained 293T cells transfected with the Notch3 construct but not the cells transfected with Notch1 or Notch2 constructs, although the anti-Notch1 and anti-Notch2 antibodies labelled the later cells respectively. 293T cells were cultured in 6-well plates and were transiently transfected by calcium phosphate precipitation with plasmids encoding for human full length Notch1, Notch2 or Notch3 cDNA. Two days after transfection, cells were harvested and lysed in RIPA buffer. Samples were adjusted to 1×SDS-Laemmli buffer, run on a 6% SDS-PAGE gel and were transferred onto nitrocellulose membranes. Immunodetection was performed by sequential incubations with 5E1 antibody or specific antibodies to human Notch1 or Notch2 and horseradish peroxidase-conjugated goat anti-mouse antibody (Jackson ImmunoResearch Laboratories Inc., West Grove, Pa., USA) followed by enhanced chemiluminescence detection (ECL; Pierce Chemical Co., Rockford, Ill., USA). The 5E1 antibody detected the full-length Notch3 precursor (~280 kDa) as well as the Notch3ECD fragment (~210 kDa) in 293Tcells transfected with the Notch3 construct. Importantly, the 5E1 antibody in 293Tcells transfected with Notch1 or Notch2 constructs detected neither Notch1 nor Notch2 protein products respectively.

EXAMPLE 3

Determination of 5E1 Relative Affinity to NOTCH3 Using Octet Binding System

Kinetic analysis was performed using the Octet RED technology from ForteBio according to the manufactures instruction. Biotinylated NOTCH3 657-848 was immobilized on streptavidin tips at a level of approximately 3 RU each. Subsequent association and dissociation of 5E1 antibody was analyzed at concentrations in the range from 333 nM to 3.3 nM. Data analysis was subsequently done using the ForteBio Data Analysis 7.0 software (FIG. 1).

EXAMPLE 4

Sequencing of 5E1

Total mRNA was extracted from the hybridoma cell pellets using RNeasy Mini Kit and following manufactures protocol (Quiagene Sciences, Valencia, Calif.) cDNA was created from the RNA by reverse-transcription with an oligo(dT) primer using Superscriptase III kit (Invitrogene, Carlsbad, Calif.). PCR reactions using variable domain primers to amplify both the VH and VL regions of the monoclonal antibody using several combinations of Ig variable domain primers (High Fidelity PCR systems, Roche)

The VH and VL products were cloned into the Invitrogen sequencing vector pCR2.1 and transformed into TOP10 cells and screened by PCR for positive transformants. Selected colonies were picked and analyzed by DNA sequencing on an ABI3130x1 Genetic Analyzer.

VH Amino Acid Sequence:
(SEQ ID NO: 11)
EIQLQQSGTVLARPGASVKMSCKAS<u>GYTFTSYWMH</u>WVKQRPGQGLE WIGA<u>IYPGNGDT</u>SYNRKFNGKAKLTAVTSTSTAYMEFSSLTNEDSAVY FCTR<u>DYGSSYDYVMDY</u>WGQGTSVTVSS VH Amino Acid Sequence:
(SEQ ID NO: 15)
DIQMTQSPSSLSASLGERVSLTCRAS<u>QDIGSS</u>LNWLQQEPDGTIKRLIY <u>ATS</u>SLDSGVPKRFSGSRSGSDYSLTISRLESEDFVDYYC<u>LQYISSPLT</u>FG

AGTKLELK

The variable domain is highlighted in BOLD.
The Complementarity Determining Regions (CDRs) are underlined as determined by the IMGT numbering system (Lefranc, M.-P. et al., Nucleic Acids Research, 27, 209-212 (1999))

EXAMPLE 5

Mice for Use in Methods

TgPAC-Notch3$^{R169C}$ (line 88) were maintained at the heterozygous state on a FVB/N background as previously described) (Joutel A, Monet-Leprêtre M, Gosele C, Baron-Menguy C, Hammes A, Schmidt S, Lemaire-Carrette B, Domenga V, Schedl A, Lacombe P, Hubner N. 2010. "Cerebrovascular dysfunction and microcirculation rarefaction precede white matter lesions in a mouse genetic model of cerebral ischemic small vessel disease." J Clin Invest 120 (2):433-45). These mice and their wild-type control littermates were bred at the animal facility on the Villemin site of Paris Diderot University (Paris, France). Mice were housed under a normal light/dark cycle (12 h) with standard rodent chow and tap water supplied ad libitum. All the experiments described here were conducted in full accordance with the guidelines of our local institutional animal care and use committee (n° 9 Lariboisière-Villemin) with every effort to minimize the number of animals used.

EXAMPLE 6

Injected Antibodies Used in Methods

5E1 monoclonal antibody (isotype IgG1) was raised against a recombinant protein derived from EGFR17-21 (amino acid residues 657-846) of human NOTCH3; it recognizes human, mouse and rat Notch3 (Joutel, A et al. 2000. "The Ectodomain of the Notch3 Receptor Accumulates within the Cerebrovasculature of CADASIL Patients." J Clin Invest 105 (5): 597-605). The 5C9E7 mouse monoclonal antibody (isotype IgG1) against human pyro-Glu Abeta and the mouse monoclonal antibody (isotype IgG1) against the hen egg white lysozyme were used as control antibodies. All antibodies were dialyzed against PBS.

EXAMPLE 7

Determination of Antibody Plasma Kinetics

TgPAC-Notch3R169C mice (n=10 males and 10 females; aged 6 weeks, weight range: 16-26 g) received a single 10 mg/kg intra peritoneal injection of 5E1. Mice were randomly assigned to 5 distinct groups (n=2 males and 2 females per group). In group 1, plasma sample was collected at 15 minutes and 24 h after the injection; in group 2, plasma was collected 30 minutes and 48 h after the injection; in group 3, plasma was collected 1 and 96 h after the injection; in group 4, plasma was collected 4 h and 1 week after the injection and in group 5, plasma was collected 8 h and 2 weeks after the injection. Five uninjected TgPAC-Notch3$^{R169C}$ mice (n=5 females; aged 6 weeks, weight range 18-22 g) were used as controls. All mice were sacrificed and tissues were harvested immediately after the second blood sampling. Antibody levels in plasma were determined. $T_{1/2}$ was determined to be 6-7 days and Cmax (4 hours) was about 500 ug/ml. Quantitation of free plasma mAb level was performed using 5E1 as standard and Notch domain coated plates.

EXAMPLE 8

Determination of In Vivo Antibody Recognition of Notch3ECD Deposits

The 5E1 and control 5C9E7 antibodies were concentrated and conjugated to the Alexa-488 molecule. At 10-12 months of age, TgPAC-Notch3R169C mice exhibit extensive Notch3ECD deposits in both the brain and peripheral vessels. Ten to twelve months-old TgPAC-Notch3R169C or wildtype mice (n=4 per treatment) were injected intraperitoneally with the 5E1 or control IgG1 antibodies (Alexa conjugated or unconjugated) at 10 mg/kg of body weight. After 3 days, mice were deeply anesthetized with sodium pentobarbital (80 mg/kg), flush-perfused transcardially with phosphate buffer phosphate (PB). Brain and peripheral tissues were harvested, frozen in liquid nitrogen and stored at −80° C. Cryostat sections (12 µm) were then analyzed by direct fluorescence or were coimmunolabeled with Alexa 488-conjugated antibodies against murine immunoglobulin (1:500, Life Technology) together with antibodies against the Nter (Ala40-Glu468) of musNotch3 (1:2000 dilution; R&D AF 1308) and detected with secondary anti-goat Alexa 594 (1:500, Life technologies) or antibodies against a recombinant rat NOTCH3 protein (aa 649-859, sequence NP_064472) (1:16,000 dilution) and detected with secondary Alexa 594 anti-rabbit (1:500, Life Technology). Sections were washed, counterstained with DAPI (1:10,000; Sigma-Aldrich) in PBS for 5 minutes at room temperature, mounted in a drop of Dako fluorescence mounting medium and subjected to epifluorescence imaging (Nikon eclipse 80i). Results are shown in FIG. 2.

EXAMPLE 9

Histology In Vivo Target Engagement

The acute target engagement of 5E1 or control egg white IgG1 was evaluated in 2 months old TgPAC-Notch3R169C mice. Mice (n=4 per treatment) were injected intraperitoneally with 10 mg antibody/kg of body weight; 72 hrs. later, mice were deeply anesthetized with sodium pentobarbital (80 mg/kg), flush-perfused transcardially with phosphate buffer phosphate (PB), the brain and kidney were harvested, frozen in liquid nitrogen and stored at −80° C. Acetone fixed cryostat serial sections (12 µm) were stained with an Alexa 594 conjugated anti-mouse antibody to visualize the murine antibody that had engaged the Notch3ECD deposits and coimmunolabeled either with the Alexa 488conjugated 5E1 or with the antibody against the N-ter of musNotch3 (1:2000 dilution; R&D AF 1308) detected with secondary anti-goat Alexa 488 conjugated IgG , or the antibody against a recombinant rat NOTCH3 protein (aa 649-859, sequence NP_064472) (1:16,000 dilution) and detected with secondary Alexa 488 anti-rabbit (1:500, Life Technology), to determine the total amount of Notch3ECD deposits. Results are shown in FIG. 2.

EXAMPLE 10

Passive Immunizations

Experimental mice were divided in two groups. For the first group, two months old TgPAC-Notch3R169C male mice were randomized and dosed weekly intraperitoneally with 10 mg/kg of 5E1 or control egg white IgG1 for four months. At the conclusion of dosing, mice (n=12-14 per treatment) were analysed for in vivo cerebrovascular reactivity or measurement of active and passive diameters of pressurized pial arteries, the brain was subsequently harvested to quantify vascular Notch3ECD and GOM deposits, and the plasma was collected to determine antibody levels. The second group included untreated TgPAC-Notch3R169C and wild type male mice (n=30) analysed at study initiation with a mean age of 2 months to determine the initial load of Notch3ECD and GOM deposits as well as the initial cerebrovascular function, and at study completion with a mean age of 6 months, to follow the extent of cerebrovascular dysfunction. Results shown in FIGS. 3 and 4.

EXAMPLE 11

Quantitative Analysis of Notch3ECD and GOM Deposits

Mice were overdosed with isoflurane, decapitated, and the brain was harvested. For immunodetection of Notch3ECD deposits, half brain was frozen in liquid nitrogen and stored at −80° C. Acetone fixed cryosections (12 µm) were stained with (1) goat polyclonal anti-Notch3ECD (1:2000 dilution; R&D AF 1308) or rabbit polyclonal antibody against a recombinant rat NOTCH3 protein (aa 649-859, sequence NP_064472) (1:16,000 dilution) (2) rabbit polyclonal anti-collagen IV (αColIV) (1:250 dilution; Novotec 20411) or rat monoclonal anti-perlecan (1:1000 dilution; clone A7L6, Millipore) and (3) FITC conjugated alpha smooth muscle actin (SMA) (1:2500 dilution, Sigma-Aldrich) followed by appropriate secondary antibodies (anti-goat Alexa 594, anti-rabbit Alexa 594, anti-rabbit Alexa 350 or anti-rat Alexa 350) (1:500, Life technologies). Stained sections were imaged using a Nikon 80i eclipse microscope at 40× magnification setting and captured using a digital camera (Nikon) and NIS Elements BR v 3.0 software (Nikon), with identical settings across compared groups.

For quantitative analysis of Notch3ECD deposits, we used the ImageJ software: the mean parenchyma background intensity value of all images was set to a fixed value, vessel borders were manually delineated and vessel area was then analyzed by the "Analyze Particles" function. Arteries were identified as SMA positively stained vessels, capillaries were defined as collagen IV or perlecan positively stained and SMA negatively stained vessels with a diameter <10 µm. The mean of 3 non consecutive sections was used to represent a Notch3ECD load for each mouse. Results are expressed as the number of deposits over the vessel area or length. All analysis were performed in a blinded manner.

For detection of GOM deposits, half brain was fixed in CARSON solution. The middle cerebral artery and surrounding brain tissue were dissected under the microscope and embedded in Epon E812 resin as previously described (Joutel A, Monet-Leprêtre M, Gosele C, Baron-Menguy C, Hammes A, Schmidt S, Lemaire-Carrette B, Domenga V, Schedl A, Lacombe P, Hubner N. 2010. "Cerebrovascular dysfunction and microcirculation rarefaction precede white matter lesions in a mouse genetic model of cerebral ischemic small vessel disease." J Clin Invest 120(2):433-45). Semi-thin sections were cut with an ultramicrotome (Leica EM EC7), stained with 1% toluidine blue and screened by light microscopy to select the region containing the middle cerebral artery. Ultrathin sections of regions of interest were cut, mounted on copper grids, contrast stained with uranyl acetate and lead citrate and examined by transmission electron microscopy (Philips CM100). Electron micrograph images were captured using a digital camera at magnification 7,400. For each mouse, an arterial ring (mean diameter 60-80 μm) was rebuild using PhotoShop. Number of GOM deposits was blind counted on the abluminal perimeter of smooth muscle cells. Results are expressed as a number of GOM deposits/100 μm and shown on FIG. 3.

EXAMPLE 12

In Vivo Analysis of Cerebrovascular Reactivity

Mice were anesthetized with isoflurane (maintenance, 2%), mice were then intubated, and artificially ventilated with an 02/N2 mixture adjusted to provide an arterial $PO_2$ of 120 to 130 mm Hg and $PC0_2$ of 33 to 36 mmHg. The femoral artery was cannulated for recording of arterial pressure, and blood sampling for blood gazes determination. Rectal temperature was maintained at 37° C., using a thermostatically controlled rectal probe connected to a heating pad. After surgery, isoflurane was gradually discontinued and anesthesia was maintained with urethane (750 mg/kg, i.p.) and α-chloralose (50 mg/kg, i.p.). The level of anesthesia was monitored by testing corneal reflexes and responses to tail pinch. The somatosensory cortex was exposed by drilling a small hole through the parietal bone (2×2 mm) the dura was removed, and the site was superfused with a modified Ringer's solution (37° C.; pH 7.3-7.4). Cerebral blood flow (CBF) was monitored in this cranial open window by using a laser Doppler flowmeter probe (Moor Instruments, MBF3-Dual, Axminster, Devon, UK), positioned stereotaxically above the brain surface and connected to a computerized data acquisition system (Powerlab, Chart). The laser Doppler flowmeter probe detects microvascular blood flow in a 1-mm3 tissue volume. The outputs of the flowmeter and blood pressure transducer were connected to a computerized data acquisition system (Powerlab, Chart). Experiments were started 30±5 minutes after the end of surgery and isoflurane discontinuation, when arterial pressure and blood gases were in a steady state. The whiskers, contralateral to the cranial window, were gently stroked for 1 minute with a cotton-tipped applicator at a frequency of 3 to 4 Hz and CBF responses to whisker stimulation were recorded. CBF responses to acetylcholine (10 μM; Sigma), bradykinin (50 μM; Sigma), the calcium ionophore A23187 (3 μM; Sigma) and NO-independent vasodilator adenosine (400 μM; Sigma) were also tested. CBF was expressed as percent increase relative to the resting level. Results shown in FIG. 4.

EXAMPLE 13

Ex vivo Analysis of Myogenic Tone and Arterial Remodeling

After overdosing with CO2, mice were decapitated and their brains were harvested. Arterial segments of the posterior cerebral artery were dissected, cannulated on two glass micropipettes in an organ chamber containing physiological salt solution (PSS) maintained at 37° C. (pH 7.4), and pressurized using an arteriograph system (Living Systems Instrumentation, Inc., VT, USA). Once prepared, arteries were allowed to stabilize for at least 30 minutes at a pressure of 50 mmHg before initiating basal tone analyses. Myogenic tone was determined by increasing intraluminal pressure in steps of 10 to 100 mmHg using a pressure-servo control pump. Vessel internal diameter was continuously recorded using a CCD camera and edge-detection software (Biopac MP150 and AcqKnowledge software, Biopac Systems Inc, CA, USA). Diameters measured in PSS were considered active diameters. At the end of each experiment, maximal dilation was obtained in nominally Ca2+-free PSS containing EGTA (2-5 mmol/L, Sigma) and sodium nitroprusside (10 μmol/L, Sigma). Pressure steps were repeated to determine the passive diameter of the arteries. Artery diameters are given in micrometers. Myogenic tone was expressed as the percentage of passive diameter ([passive diameter–active diameter]/passive diameter×100). Results shown in FIG. 4D-E.

The invention claimed is:

1. A method of preventing or treating inward remodelling and reduced myogenic tone of brain arteries in a subject in need thereof comprising administering to the subject an effective amount of an anti-Notch3 antibody or a fragment thereof having a 2 fold, 4 fold or 10 fold higher affinity to Notch 3 than to Notch 1 or Notch 2, wherein said anti-Notch3 antibody or fragment thereof binds to an extracellular domain of NOTCH3 (Notch3ECD) deposit and wherein the anti-Notch3 antibody or fragment thereof comprises all of
   a heavy chain variable region H-CDR1 comprising the amino acid sequence of SEQ ID NO: 8;
   a heavy chain variable region H-CDR2 comprising the amino acid sequence of SEQ ID NO: 9;
   a heavy chain variable region H-CDR3 comprising the amino acid sequence of SEQ ID NO: 10;
   a light chain variable region L-CDR1 comprising the amino acid sequence of SEQ ID NO: 12;
   a light chain variable region L-CDR2 comprising the amino acid sequence of SEQ ID NO: 13; and
   a light chain variable region L-CDR3 comprising the amino acid sequence of SEQ ID NO: 14.

2. The method according to claim 1, wherein said anti-Notch3 antibody or fragment thereof does not bind Notch 1 or Notch 2.

3. The method according to claim 1, wherein said anti-Notch3 antibody or fragment thereof binds to an epitope comprising amino acids 40-1643 of human Notch3 (SEQ ID NO: 3).

4. The method according to claim 3 wherein said anti-Notch3 antibody or fragment thereof binds to an epitope comprised in amino acids 657-846 of human Notch3 (SEQ ID NO: 7).

5. The method according to claim 1, wherein said anti-Notch3 antibody or fragment thereof is isolated.

6. The method according to claim 1, wherein said anti-Notch3 antibody or fragment thereof comprises both a heavy chain variable region comprising the amino acid sequence of SEQ ID NO: 11 and a light chain variable domain comprising the amino acid sequence of SEQ ID NO: 15.

7. The method according to claim 1, wherein said anti-Notch3 antibody or fragment thereof is humanized.

8. The method according to claim 1, wherein the treatment is chronic.

9. The method according to claim 8, wherein the chronic treatment is for at least: 2 weeks, 1 month, 6 months, or 1 year.

10. The method of claim 1, wherein the subject suffers from cerebral autosomal dominant arteriopathy with subcortical infarcts and leukoencephalopathy (CADASIL).

* * * * *

SEQUENCE LISTING

```
<160> NUMBER OF SEQ ID NOS: 15

<210> SEQ ID NO 1
<211> LENGTH: 2321
<212> TYPE: PRT
<213> ORGANISM: homo sapiens

<400> SEQUENCE: 1

Met Gly Pro Gly Ala Arg Gly Arg Arg Arg Arg Arg Pro Met Ser
1               5                   10                  15

Pro Pro Pro Pro Pro Pro Val Arg Ala Leu Pro Leu Leu Leu Leu
                20                  25                  30

Leu Ala Gly Pro Gly Ala Ala Ala Pro Pro Cys Leu Asp Gly Ser Pro
                35                  40                  45

Cys Ala Asn Gly Gly Arg Cys Thr Gln Leu Pro Ser Arg Glu Ala Ala
    50                  55                      60

Cys Leu Cys Pro Pro Gly Trp Val Gly Glu Arg Cys Gln Leu Glu Asp
65                  70                  75                  80

Pro Cys His Ser Gly Pro Cys Ala Gly Arg Gly Val Cys Gln Ser Ser
                85                  90                  95

Val Val Ala Gly Thr Ala Arg Phe Ser Cys Arg Cys Pro Arg Gly Phe
                100                 105                 110

Arg Gly Pro Asp Cys Ser Leu Pro Asp Pro Cys Leu Ser Ser Pro Cys
```

```
            115                 120                 125
Ala His Gly Ala Arg Cys Ser Val Gly Pro Asp Gly Arg Phe Leu Cys
    130                 135                 140

Ser Cys Pro Pro Gly Tyr Gln Gly Arg Ser Cys Arg Ser Asp Val Asp
145                 150                 155                 160

Glu Cys Arg Val Gly Glu Pro Cys Arg His Gly Gly Thr Cys Leu Asn
                165                 170                 175

Thr Pro Gly Ser Phe Arg Cys Gln Cys Pro Ala Gly Tyr Thr Gly Pro
            180                 185                 190

Leu Cys Glu Asn Pro Ala Val Pro Cys Ala Pro Ser Pro Cys Arg Asn
        195                 200                 205

Gly Gly Thr Cys Arg Gln Ser Gly Asp Leu Thr Tyr Asp Cys Ala Cys
    210                 215                 220

Leu Pro Gly Phe Glu Gly Gln Asn Cys Glu Val Asn Val Asp Asp Cys
225                 230                 235                 240

Pro Gly His Arg Cys Leu Asn Gly Gly Thr Cys Val Asp Gly Val Asn
                245                 250                 255

Thr Tyr Asn Cys Gln Cys Pro Pro Glu Trp Thr Gly Gln Phe Cys Thr
            260                 265                 270

Glu Asp Val Asp Glu Cys Gln Leu Gln Pro Asn Ala Cys His Asn Gly
        275                 280                 285

Gly Thr Cys Phe Asn Thr Leu Gly Gly His Ser Cys Val Cys Val Asn
    290                 295                 300

Gly Trp Thr Gly Glu Ser Cys Ser Gln Asn Ile Asp Asp Cys Ala Thr
305                 310                 315                 320

Ala Val Cys Phe His Gly Ala Thr Cys His Asp Arg Val Ala Ser Phe
                325                 330                 335

Tyr Cys Ala Cys Pro Met Gly Lys Thr Gly Leu Leu Cys His Leu Asp
            340                 345                 350

Asp Ala Cys Val Ser Asn Pro Cys His Glu Asp Ala Ile Cys Asp Thr
        355                 360                 365

Asn Pro Val Asn Gly Arg Ala Ile Cys Thr Cys Pro Pro Gly Phe Thr
    370                 375                 380

Gly Gly Ala Cys Asp Gln Asp Val Asp Glu Cys Ser Ile Gly Ala Asn
385                 390                 395                 400

Pro Cys Glu His Leu Gly Arg Cys Val Asn Thr Gln Gly Ser Phe Leu
                405                 410                 415

Cys Gln Cys Gly Arg Gly Tyr Thr Gly Pro Arg Cys Glu Thr Asp Val
            420                 425                 430

Asn Glu Cys Leu Ser Gly Pro Cys Arg Asn Gln Ala Thr Cys Leu Asp
        435                 440                 445

Arg Ile Gly Gln Phe Thr Cys Ile Cys Met Ala Gly Phe Thr Gly Thr
    450                 455                 460

Tyr Cys Glu Val Asp Ile Asp Glu Cys Gln Ser Ser Pro Cys Val Asn
465                 470                 475                 480

Gly Gly Val Cys Lys Asp Arg Val Asn Gly Phe Ser Cys Thr Cys Pro
                485                 490                 495

Ser Gly Phe Ser Gly Ser Thr Cys Gln Leu Asp Val Asp Glu Cys Ala
            500                 505                 510

Ser Thr Pro Cys Arg Asn Gly Ala Lys Cys Val Asp Gln Pro Asp Gly
        515                 520                 525

Tyr Glu Cys Arg Cys Ala Glu Gly Phe Glu Gly Thr Leu Cys Asp Arg
    530                 535                 540
```

-continued

```
Asn Val Asp Asp Cys Ser Pro Asp Pro Cys His His Gly Arg Cys Val
545                 550                 555                 560

Asp Gly Ile Ala Ser Phe Ser Cys Ala Cys Ala Pro Gly Tyr Thr Gly
                565                 570                 575

Thr Arg Cys Glu Ser Gln Val Asp Glu Cys Arg Ser Gln Pro Cys Arg
            580                 585                 590

His Gly Gly Lys Cys Leu Asp Leu Val Asp Lys Tyr Leu Cys Arg Cys
        595                 600                 605

Pro Ser Gly Thr Thr Gly Val Asn Cys Glu Val Asn Ile Asp Asp Cys
610                 615                 620

Ala Ser Asn Pro Cys Thr Phe Gly Val Cys Arg Asp Gly Ile Asn Arg
625                 630                 635                 640

Tyr Asp Cys Val Cys Gln Pro Gly Phe Thr Gly Pro Leu Cys Asn Val
                645                 650                 655

Glu Ile Asn Glu Cys Ala Ser Ser Pro Cys Gly Glu Gly Gly Ser Cys
            660                 665                 670

Val Asp Gly Glu Asn Gly Phe Arg Cys Leu Cys Pro Pro Gly Ser Leu
        675                 680                 685

Pro Pro Leu Cys Leu Pro Pro Ser His Pro Cys Ala His Glu Pro Cys
690                 695                 700

Ser His Gly Ile Cys Tyr Asp Ala Pro Gly Gly Phe Arg Cys Val Cys
705                 710                 715                 720

Glu Pro Gly Trp Ser Gly Pro Arg Cys Ser Gln Ser Leu Ala Arg Asp
                725                 730                 735

Ala Cys Glu Ser Gln Pro Cys Arg Ala Gly Gly Thr Cys Ser Ser Asp
            740                 745                 750

Gly Met Gly Phe His Cys Thr Cys Pro Pro Gly Val Gln Gly Arg Gln
        755                 760                 765

Cys Glu Leu Leu Ser Pro Cys Thr Pro Asn Pro Cys Glu His Gly Gly
770                 775                 780

Arg Cys Glu Ser Ala Pro Gly Gln Leu Pro Val Cys Ser Cys Pro Gln
785                 790                 795                 800

Gly Trp Gln Gly Pro Arg Cys Gln Asp Val Asp Glu Cys Ala Gly
                805                 810                 815

Pro Ala Pro Cys Gly Pro His Gly Ile Cys Thr Asn Leu Ala Gly Ser
            820                 825                 830

Phe Ser Cys Thr Cys His Gly Gly Tyr Thr Gly Pro Ser Cys Asp Gln
        835                 840                 845

Asp Ile Asn Asp Cys Asp Pro Asn Pro Cys Leu Asn Gly Gly Ser Cys
850                 855                 860

Gln Asp Gly Val Gly Ser Phe Ser Cys Ser Cys Leu Pro Gly Phe Ala
865                 870                 875                 880

Gly Pro Arg Cys Ala Arg Asp Val Asp Glu Cys Leu Ser Asn Pro Cys
            885                 890                 895

Gly Pro Gly Thr Cys Thr Asp His Val Ala Ser Phe Thr Cys Thr Cys
        900                 905                 910

Pro Pro Gly Tyr Gly Gly Phe His Cys Glu Gln Asp Leu Pro Asp Cys
915                 920                 925

Ser Pro Ser Ser Cys Phe Asn Gly Gly Thr Cys Val Asp Gly Val Asn
930                 935                 940

Ser Phe Ser Cys Leu Cys Arg Pro Gly Tyr Thr Gly Ala His Cys Gln
945                 950                 955                 960
```

```
His Glu Ala Asp Pro Cys Leu Ser Arg Pro Cys Leu His Gly Gly Val
            965                 970                 975

Cys Ser Ala Ala His Pro Gly Phe Arg Cys Thr Cys Leu Glu Ser Phe
            980                 985                 990

Thr Gly Pro Gln Cys Gln Thr Leu Val Asp Trp Cys Ser Arg Gln Pro
            995                1000                1005

Cys Gln Asn Gly Gly Arg Cys Val Gln Thr Gly Ala Tyr Cys Leu
        1010                1015                1020

Cys Pro Pro Gly Trp Ser Gly Arg Leu Cys Asp Ile Arg Ser Leu
        1025                1030                1035

Pro Cys Arg Glu Ala Ala Ala Gln Ile Gly Val Arg Leu Glu Gln
        1040                1045                1050

Leu Cys Gln Ala Gly Gly Gln Cys Val Asp Glu Asp Ser Ser His
        1055                1060                1065

Tyr Cys Val Cys Pro Glu Gly Arg Thr Gly Ser His Cys Glu Gln
        1070                1075                1080

Glu Val Asp Pro Cys Leu Ala Gln Pro Cys Gln His Gly Gly Thr
        1085                1090                1095

Cys Arg Gly Tyr Met Gly Gly Tyr Met Cys Glu Cys Leu Pro Gly
        1100                1105                1110

Tyr Asn Gly Asp Asn Cys Glu Asp Val Asp Glu Cys Ala Ser
        1115                1120                1125

Gln Pro Cys Gln His Gly Gly Ser Cys Ile Asp Leu Val Ala Arg
        1130                1135                1140

Tyr Leu Cys Ser Cys Pro Pro Gly Thr Leu Gly Val Leu Cys Glu
        1145                1150                1155

Ile Asn Glu Asp Asp Cys Gly Pro Gly Pro Pro Leu Asp Ser Gly
        1160                1165                1170

Pro Arg Cys Leu His Asn Gly Thr Cys Val Asp Leu Val Gly Gly
        1175                1180                1185

Phe Arg Cys Thr Cys Pro Pro Gly Tyr Thr Gly Leu Arg Cys Glu
        1190                1195                1200

Ala Asp Ile Asn Glu Cys Arg Ser Gly Ala Cys His Ala Ala His
        1205                1210                1215

Thr Arg Asp Cys Leu Gln Asp Pro Gly Gly Gly Phe Arg Cys Leu
        1220                1225                1230

Cys His Ala Gly Phe Ser Gly Pro Arg Cys Gln Thr Val Leu Ser
        1235                1240                1245

Pro Cys Glu Ser Gln Pro Cys Gln His Gly Gly Gln Cys Arg Pro
        1250                1255                1260

Ser Pro Gly Pro Gly Gly Gly Leu Thr Phe Thr Cys His Cys Ala
        1265                1270                1275

Gln Pro Phe Trp Gly Pro Arg Cys Glu Arg Val Ala Arg Ser Cys
        1280                1285                1290

Arg Glu Leu Gln Cys Pro Val Gly Val Pro Cys Gln Gln Thr Pro
        1295                1300                1305

Arg Gly Pro Arg Cys Ala Cys Pro Pro Gly Leu Ser Gly Pro Ser
        1310                1315                1320

Cys Arg Ser Phe Pro Gly Ser Pro Pro Gly Ala Ser Asn Ala Ser
        1325                1330                1335

Cys Ala Ala Ala Pro Cys Leu His Gly Gly Ser Cys Arg Pro Ala
        1340                1345                1350

Pro Leu Ala Pro Phe Phe Arg Cys Ala Cys Ala Gln Gly Trp Thr
```

-continued

|      | 1355 |      |      | 1360 |      |      | 1365 |      |      |
|------|------|------|------|------|------|------|------|------|------|

Gly Pro Arg Cys Glu Ala Pro Ala Ala Pro Glu Val Ser Glu
         1370              1375              1380

Glu Pro Arg Cys Pro Arg Ala Cys Gln Ala Lys Arg Gly Asp
         1385              1390              1395

Gln Arg Cys Asp Arg Glu Cys Asn Ser Pro Gly Cys Gly Trp Asp
         1400              1405              1410

Gly Gly Asp Cys Ser Leu Ser Val Gly Asp Pro Trp Arg Gln Cys
         1415              1420              1425

Glu Ala Leu Gln Cys Trp Arg Leu Phe Asn Asn Ser Arg Cys Asp
         1430              1435              1440

Pro Ala Cys Ser Ser Pro Ala Cys Leu Tyr Asp Asn Phe Asp Cys
         1445              1450              1455

His Ala Gly Gly Arg Glu Arg Thr Cys Asn Pro Val Tyr Glu Lys
         1460              1465              1470

Tyr Cys Ala Asp His Phe Ala Asp Gly Arg Cys Asp Gln Gly Cys
         1475              1480              1485

Asn Thr Glu Glu Cys Gly Trp Asp Gly Leu Asp Cys Ala Ser Glu
         1490              1495              1500

Val Pro Ala Leu Leu Ala Arg Gly Val Leu Val Leu Thr Val Leu
         1505              1510              1515

Leu Pro Pro Glu Glu Leu Leu Arg Ser Ser Ala Asp Phe Leu Gln
         1520              1525              1530

Arg Leu Ser Ala Ile Leu Arg Thr Ser Leu Arg Phe Arg Leu Asp
         1535              1540              1545

Ala His Gly Gln Ala Met Val Phe Pro Tyr His Arg Pro Ser Pro
         1550              1555              1560

Gly Ser Glu Pro Arg Ala Arg Arg Glu Leu Ala Pro Glu Val Ile
         1565              1570              1575

Gly Ser Val Val Met Leu Glu Ile Asp Asn Arg Leu Cys Leu Gln
         1580              1585              1590

Ser Pro Glu Asn Asp His Cys Phe Pro Asp Ala Gln Ser Ala Ala
         1595              1600              1605

Asp Tyr Leu Gly Ala Leu Ser Ala Val Glu Arg Leu Asp Phe Pro
         1610              1615              1620

Tyr Pro Leu Arg Asp Val Arg Gly Glu Pro Leu Glu Pro Pro Glu
         1625              1630              1635

Pro Ser Val Pro Leu Leu Pro Leu Leu Val Ala Gly Ala Val Leu
         1640              1645              1650

Leu Leu Val Ile Leu Val Leu Gly Val Met Val Ala Arg Arg Lys
         1655              1660              1665

Arg Glu His Ser Thr Leu Trp Phe Pro Glu Gly Phe Ser Leu His
         1670              1675              1680

Lys Asp Val Ala Ser Gly His Lys Gly Arg Arg Glu Pro Val Gly
         1685              1690              1695

Gln Asp Ala Leu Gly Met Lys Asn Met Ala Lys Gly Glu Ser Leu
         1700              1705              1710

Met Gly Glu Val Ala Thr Asp Trp Met Asp Thr Glu Cys Pro Glu
         1715              1720              1725

Ala Lys Arg Leu Lys Val Glu Glu Pro Gly Met Gly Ala Glu Glu
         1730              1735              1740

Ala Val Asp Cys Arg Gln Trp Thr Gln His His Leu Val Ala Ala
         1745              1750              1755

```
-continued

Asp Ile Arg Val Ala Pro Ala Met Ala Leu Thr Pro Pro Gln Gly
    1760            1765                1770

Asp Ala Asp Ala Asp Gly Met Asp Val Asn Val Arg Gly Pro Asp
    1775            1780                1785

Gly Phe Thr Pro Leu Met Leu Ala Ser Phe Cys Gly Gly Ala Leu
    1790            1795                1800

Glu Pro Met Pro Thr Glu Glu Asp Glu Ala Asp Thr Ser Ala
    1805            1810                1815

Ser Ile Ile Ser Asp Leu Ile Cys Gln Gly Ala Gln Leu Gly Ala
    1820            1825                1830

Arg Thr Asp Arg Thr Gly Glu Thr Ala Leu His Leu Ala Ala Arg
    1835            1840                1845

Tyr Ala Arg Ala Asp Ala Ala Lys Arg Leu Leu Asp Ala Gly Ala
    1850            1855                1860

Asp Thr Asn Ala Gln Asp His Ser Gly Arg Thr Pro Leu His Thr
    1865            1870                1875

Ala Val Thr Ala Asp Ala Gln Gly Val Phe Gln Ile Leu Ile Arg
    1880            1885                1890

Asn Arg Ser Thr Asp Leu Asp Ala Arg Met Ala Asp Gly Ser Thr
    1895            1900                1905

Ala Leu Ile Leu Ala Ala Arg Leu Ala Val Glu Gly Met Val Glu
    1910            1915                1920

Glu Leu Ile Ala Ser His Ala Asp Val Asn Ala Val Asp Glu Leu
    1925            1930                1935

Gly Lys Ser Ala Leu His Trp Ala Ala Ala Val Asn Asn Val Glu
    1940            1945                1950

Ala Thr Leu Ala Leu Leu Lys Asn Gly Ala Asn Lys Asp Met Gln
    1955            1960                1965

Asp Ser Lys Glu Glu Thr Pro Leu Phe Leu Ala Ala Arg Glu Gly
    1970            1975                1980

Ser Tyr Glu Ala Ala Lys Leu Leu Leu Asp His Phe Ala Asn Arg
    1985            1990                1995

Glu Ile Thr Asp His Leu Asp Arg Leu Pro Arg Asp Val Ala Gln
    2000            2005                2010

Glu Arg Leu His Gln Asp Ile Val Arg Leu Leu Asp Gln Pro Ser
    2015            2020                2025

Gly Pro Arg Ser Pro Pro Gly Pro His Gly Leu Gly Pro Leu Leu
    2030            2035                2040

Cys Pro Pro Gly Ala Phe Leu Pro Gly Leu Lys Ala Ala Gln Ser
    2045            2050                2055

Gly Ser Lys Lys Ser Arg Arg Pro Pro Gly Lys Ala Gly Leu Gly
    2060            2065                2070

Pro Gln Gly Pro Arg Gly Arg Gly Lys Lys Leu Thr Leu Ala Cys
    2075            2080                2085

Pro Gly Pro Leu Ala Asp Ser Ser Val Thr Leu Ser Pro Val Asp
    2090            2095                2100

Ser Leu Asp Ser Pro Arg Pro Phe Gly Gly Pro Ala Ser Pro
    2105            2110                2115

Gly Gly Phe Pro Leu Glu Gly Pro Tyr Ala Ala Ala Thr Ala Thr
    2120            2125                2130

Ala Val Ser Leu Ala Gln Leu Gly Gly Pro Gly Arg Ala Gly Leu
    2135            2140                2145
```

-continued

```
Gly Arg Gln Pro Pro Gly Gly Cys Val Leu Ser Leu Gly Leu Leu
    2150            2155                2160

Asn Pro Val Ala Val Pro Leu Asp Trp Ala Arg Leu Pro Pro Pro
    2165            2170                2175

Ala Pro Pro Gly Pro Ser Phe Leu Leu Pro Leu Ala Pro Gly Pro
    2180            2185                2190

Gln Leu Leu Asn Pro Gly Thr Pro Val Ser Pro Gln Glu Arg Pro
    2195            2200                2205

Pro Pro Tyr Leu Ala Val Pro Gly His Gly Glu Glu Tyr Pro Ala
    2210            2215                2220

Ala Gly Ala His Ser Ser Pro Pro Lys Ala Arg Phe Leu Arg Val
    2225            2230                2235

Pro Ser Glu His Pro Tyr Leu Thr Pro Ser Pro Glu Ser Pro Glu
    2240            2245                2250

His Trp Ala Ser Pro Ser Pro Pro Ser Leu Ser Asp Trp Ser Glu
    2255            2260                2265

Ser Thr Pro Ser Pro Ala Thr Ala Thr Gly Ala Met Ala Thr Thr
    2270            2275                2280

Thr Gly Ala Leu Pro Ala Gln Pro Leu Pro Leu Ser Val Pro Ser
    2285            2290                2295

Ser Leu Ala Gln Ala Gln Thr Gln Leu Gly Pro Gln Pro Glu Val
    2300            2305                2310

Thr Pro Lys Arg Gln Val Leu Ala
    2315            2320

<210> SEQ ID NO 2
<211> LENGTH: 39
<212> TYPE: PRT
<213> ORGANISM: homo sapiens

<400> SEQUENCE: 2

Met Gly Pro Gly Ala Arg Gly Arg Arg Arg Arg Arg Pro Met Ser
1               5                   10                  15

Pro Pro Pro Pro Pro Pro Pro Val Arg Ala Leu Pro Leu Leu Leu
                20                  25                  30

Leu Ala Gly Pro Gly Ala Ala Ala
            35

<210> SEQ ID NO 3
<211> LENGTH: 1604
<212> TYPE: PRT
<213> ORGANISM: homo sapiens

<400> SEQUENCE: 3

Ala Pro Pro Cys Leu Asp Gly Ser Pro Cys Ala Asn Gly Gly Arg Cys
1               5                   10                  15

Thr Gln Leu Pro Ser Arg Glu Ala Ala Cys Leu Cys Pro Pro Gly Trp
                20                  25                  30

Val Gly Glu Arg Cys Gln Leu Glu Asp Pro Cys His Ser Gly Pro Cys
            35                  40                  45

Ala Gly Arg Gly Val Cys Gln Ser Ser Val Val Ala Gly Thr Ala Arg
        50                  55                  60

Phe Ser Cys Arg Cys Pro Arg Gly Phe Arg Gly Pro Asp Cys Ser Leu
65                  70                  75                  80

Pro Asp Pro Cys Leu Ser Ser Pro Cys Ala His Gly Ala Arg Cys Ser
                85                  90                  95
```

```
Val Gly Pro Asp Gly Arg Phe Leu Cys Ser Cys Pro Gly Tyr Gln
            100                 105                 110

Gly Arg Ser Cys Arg Ser Asp Val Asp Glu Cys Arg Val Gly Glu Pro
        115                 120                 125

Cys Arg His Gly Gly Thr Cys Leu Asn Thr Pro Gly Ser Phe Arg Cys
        130                 135                 140

Gln Cys Pro Ala Gly Tyr Thr Gly Pro Leu Cys Glu Asn Pro Ala Val
145                 150                 155                 160

Pro Cys Ala Pro Ser Pro Cys Arg Asn Gly Gly Thr Cys Arg Gln Ser
                165                 170                 175

Gly Asp Leu Thr Tyr Asp Cys Ala Cys Leu Pro Gly Phe Glu Gly Gln
            180                 185                 190

Asn Cys Glu Val Asn Val Asp Asp Cys Pro Gly His Arg Cys Leu Asn
        195                 200                 205

Gly Gly Thr Cys Val Asp Gly Val Asn Thr Tyr Asn Cys Gln Cys Pro
        210                 215                 220

Pro Glu Trp Thr Gly Gln Phe Cys Thr Glu Asp Val Asp Glu Cys Gln
225                 230                 235                 240

Leu Gln Pro Asn Ala Cys His Asn Gly Gly Thr Cys Phe Asn Thr Leu
                245                 250                 255

Gly Gly His Ser Cys Val Cys Val Asn Gly Trp Thr Gly Glu Ser Cys
            260                 265                 270

Ser Gln Asn Ile Asp Asp Cys Ala Thr Ala Val Cys Phe His Gly Ala
        275                 280                 285

Thr Cys His Asp Arg Val Ala Ser Phe Tyr Cys Ala Cys Pro Met Gly
        290                 295                 300

Lys Thr Gly Leu Leu Cys His Leu Asp Asp Ala Cys Val Ser Asn Pro
305                 310                 315                 320

Cys His Glu Asp Ala Ile Cys Asp Thr Asn Pro Val Asn Gly Arg Ala
                325                 330                 335

Ile Cys Thr Cys Pro Pro Gly Phe Thr Gly Gly Ala Cys Asp Gln Asp
            340                 345                 350

Val Asp Glu Cys Ser Ile Gly Ala Asn Pro Cys Glu His Leu Gly Arg
        355                 360                 365

Cys Val Asn Thr Gln Gly Ser Phe Leu Cys Gln Cys Gly Arg Gly Tyr
        370                 375                 380

Thr Gly Pro Arg Cys Glu Thr Asp Val Asn Glu Cys Leu Ser Gly Pro
385                 390                 395                 400

Cys Arg Asn Gln Ala Thr Cys Leu Asp Arg Ile Gly Gln Phe Thr Cys
                405                 410                 415

Ile Cys Met Ala Gly Phe Thr Gly Thr Tyr Cys Glu Val Asp Ile Asp
            420                 425                 430

Glu Cys Gln Ser Ser Pro Cys Val Asn Gly Gly Val Cys Lys Asp Arg
        435                 440                 445

Val Asn Gly Phe Ser Cys Thr Cys Pro Ser Gly Phe Ser Gly Ser Thr
        450                 455                 460

Cys Gln Leu Asp Val Asp Glu Cys Ala Ser Thr Pro Cys Arg Asn Gly
465                 470                 475                 480

Ala Lys Cys Val Asp Gln Pro Asp Gly Tyr Glu Cys Arg Cys Ala Glu
                485                 490                 495

Gly Phe Glu Gly Thr Leu Cys Asp Arg Asn Val Asp Asp Cys Ser Pro
            500                 505                 510

Asp Pro Cys His His Gly Arg Cys Val Asp Gly Ile Ala Ser Phe Ser
```

```
                515                 520                 525
Cys Ala Cys Ala Pro Gly Tyr Thr Gly Thr Arg Cys Glu Ser Gln Val
    530                 535                 540

Asp Glu Cys Arg Ser Gln Pro Cys Arg His Gly Gly Lys Cys Leu Asp
545                 550                 555                 560

Leu Val Asp Lys Tyr Leu Cys Arg Cys Pro Ser Gly Thr Thr Gly Val
                565                 570                 575

Asn Cys Glu Val Asn Ile Asp Asp Cys Ala Ser Asn Pro Cys Thr Phe
            580                 585                 590

Gly Val Cys Arg Asp Gly Ile Asn Arg Tyr Asp Cys Val Cys Gln Pro
        595                 600                 605

Gly Phe Thr Gly Pro Leu Cys Asn Val Glu Ile Asn Glu Cys Ala Ser
    610                 615                 620

Ser Pro Cys Gly Glu Gly Gly Ser Cys Val Asp Gly Glu Asn Gly Phe
625                 630                 635                 640

Arg Cys Leu Cys Pro Pro Gly Ser Leu Pro Leu Cys Leu Pro Pro
                645                 650                 655

Ser His Pro Cys Ala His Glu Pro Cys Ser His Gly Ile Cys Tyr Asp
            660                 665                 670

Ala Pro Gly Gly Phe Arg Cys Val Cys Glu Pro Gly Trp Ser Gly Pro
        675                 680                 685

Arg Cys Ser Gln Ser Leu Ala Arg Asp Ala Cys Glu Ser Gln Pro Cys
    690                 695                 700

Arg Ala Gly Gly Thr Cys Ser Ser Asp Gly Met Gly Phe His Cys Thr
705                 710                 715                 720

Cys Pro Pro Gly Val Gln Gly Arg Gln Cys Glu Leu Leu Ser Pro Cys
                725                 730                 735

Thr Pro Asn Pro Cys Glu His Gly Gly Arg Cys Glu Ser Ala Pro Gly
            740                 745                 750

Gln Leu Pro Val Cys Ser Cys Pro Gln Gly Trp Gln Gly Pro Arg Cys
        755                 760                 765

Gln Gln Asp Val Asp Glu Cys Ala Gly Pro Ala Pro Cys Gly Pro His
    770                 775                 780

Gly Ile Cys Thr Asn Leu Ala Gly Ser Phe Ser Cys Thr Cys His Gly
785                 790                 795                 800

Gly Tyr Thr Gly Pro Ser Cys Asp Gln Asp Ile Asn Asp Cys Asp Pro
                805                 810                 815

Asn Pro Cys Leu Asn Gly Gly Ser Cys Gln Asp Gly Val Gly Ser Phe
            820                 825                 830

Ser Cys Ser Cys Leu Pro Gly Phe Ala Gly Pro Arg Cys Ala Arg Asp
        835                 840                 845

Val Asp Glu Cys Leu Ser Asn Pro Cys Gly Pro Gly Thr Cys Thr Asp
    850                 855                 860

His Val Ala Ser Phe Thr Cys Thr Cys Pro Pro Gly Tyr Gly Gly Phe
865                 870                 875                 880

His Cys Glu Gln Asp Leu Pro Asp Cys Ser Pro Ser Ser Cys Phe Asn
                885                 890                 895

Gly Gly Thr Cys Val Asp Gly Val Asn Ser Phe Ser Cys Leu Cys Arg
            900                 905                 910

Pro Gly Tyr Thr Gly Ala His Cys Gln His Glu Ala Asp Pro Cys Leu
        915                 920                 925

Ser Arg Pro Cys Leu His Gly Gly Val Cys Ser Ala Ala His Pro Gly
    930                 935                 940
```

-continued

```
Phe Arg Cys Thr Cys Leu Glu Ser Phe Thr Gly Pro Gln Cys Gln Thr
945                 950                 955                 960

Leu Val Asp Trp Cys Ser Arg Gln Pro Cys Gln Asn Gly Gly Arg Cys
                965                 970                 975

Val Gln Thr Gly Ala Tyr Cys Leu Cys Pro Pro Gly Trp Ser Gly Arg
            980                 985                 990

Leu Cys Asp Ile Arg Ser Leu Pro  Cys Arg Glu Ala Ala  Ala Gln Ile
        995                 1000                 1005

Gly Val  Arg Leu Glu Gln Leu  Cys Gln Ala Gly Gly  Gln Cys Val
    1010             1015                 1020

Asp Glu  Asp Ser Ser His Tyr  Cys Val Cys Pro Glu  Gly Arg Thr
    1025                 1030                 1035

Gly Ser  His Cys Glu Gln Glu  Val Asp Pro Cys Leu  Ala Gln Pro
    1040                 1045                 1050

Cys Gln  His Gly Gly Thr Cys  Arg Gly Tyr Met Gly  Gly Tyr Met
    1055                 1060                 1065

Cys Glu  Cys Leu Pro Gly Tyr  Asn Gly Asp Asn Cys  Glu Asp Asp
    1070                 1075                 1080

Val Asp  Glu Cys Ala Ser Gln  Pro Cys Gln His Gly  Gly Ser Cys
    1085                 1090                 1095

Ile Asp  Leu Val Ala Arg Tyr  Leu Cys Ser Cys Pro  Pro Gly Thr
    1100                 1105                 1110

Leu Gly  Val Leu Cys Glu Ile  Asn Glu Asp Asp Cys  Gly Pro Gly
    1115                 1120                 1125

Pro Pro  Leu Asp Ser Gly Pro  Arg Cys Leu His Asn  Gly Thr Cys
    1130                 1135                 1140

Val Asp  Leu Val Gly Gly Phe  Arg Cys Thr Cys Pro  Pro Gly Tyr
    1145                 1150                 1155

Thr Gly  Leu Arg Cys Glu Ala  Asp Ile Asn Glu Cys  Arg Ser Gly
    1160                 1165                 1170

Ala Cys  His Ala Ala His Thr  Arg Asp Cys Leu Gln  Asp Pro Gly
    1175                 1180                 1185

Gly Gly  Phe Arg Cys Leu Cys  His Ala Gly Phe Ser  Gly Pro Arg
    1190                 1195                 1200

Cys Gln  Thr Val Leu Ser Pro  Cys Glu Ser Gln Pro  Cys Gln His
    1205                 1210                 1215

Gly Gly  Gln Cys Arg Pro Ser  Pro Gly Pro Gly Gly  Gly Leu Thr
    1220                 1225                 1230

Phe Thr  Cys His Cys Ala Gln  Pro Phe Trp Gly Pro  Arg Cys Glu
    1235                 1240                 1245

Arg Val  Ala Arg Ser Cys Arg  Glu Leu Gln Cys Pro  Val Gly Val
    1250                 1255                 1260

Pro Cys  Gln Gln Thr Pro Arg  Gly Pro Arg Cys Ala  Cys Pro Pro
    1265                 1270                 1275

Gly Leu  Ser Gly Pro Ser Cys  Arg Ser Phe Pro Gly  Ser Pro Pro
    1280                 1285                 1290

Gly Ala  Ser Asn Ala Ser Cys  Ala Ala Ala Pro Cys  Leu His Gly
    1295                 1300                 1305

Gly Ser  Cys Arg Pro Ala Pro  Leu Ala Pro Phe Phe  Arg Cys Ala
    1310                 1315                 1320

Cys Ala  Gln Gly Trp Thr Gly  Pro Arg Cys Glu Ala  Pro Ala Ala
    1325                 1330                 1335
```

-continued

Ala Pro Glu Val Ser Glu Pro Arg Cys Pro Arg Ala Ala Cys
    1340                1345                1350

Gln Ala Lys Arg Gly Asp Gln Arg Cys Asp Arg Glu Cys Asn Ser
    1355                1360                1365

Pro Gly Cys Gly Trp Asp Gly Gly Asp Cys Ser Leu Ser Val Gly
    1370                1375                1380

Asp Pro Trp Arg Gln Cys Glu Ala Leu Gln Cys Trp Arg Leu Phe
    1385                1390                1395

Asn Asn Ser Arg Cys Asp Pro Ala Cys Ser Ser Pro Ala Cys Leu
    1400                1405                1410

Tyr Asp Asn Phe Asp Cys His Ala Gly Gly Arg Glu Arg Thr Cys
    1415                1420                1425

Asn Pro Val Tyr Glu Lys Tyr Cys Ala Asp His Phe Ala Asp Gly
    1430                1435                1440

Arg Cys Asp Gln Gly Cys Asn Thr Glu Glu Cys Gly Trp Asp Gly
    1445                1450                1455

Leu Asp Cys Ala Ser Glu Val Pro Ala Leu Leu Ala Arg Gly Val
    1460                1465                1470

Leu Val Leu Thr Val Leu Leu Pro Pro Glu Glu Leu Leu Arg Ser
    1475                1480                1485

Ser Ala Asp Phe Leu Gln Arg Leu Ser Ala Ile Leu Arg Thr Ser
    1490                1495                1500

Leu Arg Phe Arg Leu Asp Ala His Gly Gln Ala Met Val Phe Pro
    1505                1510                1515

Tyr His Arg Pro Ser Pro Gly Ser Glu Pro Arg Ala Arg Arg Glu
    1520                1525                1530

Leu Ala Pro Glu Val Ile Gly Ser Val Val Met Leu Glu Ile Asp
    1535                1540                1545

Asn Arg Leu Cys Leu Gln Ser Pro Glu Asn Asp His Cys Phe Pro
    1550                1555                1560

Asp Ala Gln Ser Ala Ala Asp Tyr Leu Gly Ala Leu Ser Ala Val
    1565                1570                1575

Glu Arg Leu Asp Phe Pro Tyr Pro Leu Arg Asp Val Arg Gly Glu
    1580                1585                1590

Pro Leu Glu Pro Pro Glu Pro Ser Val Pro Leu
    1595                1600

<210> SEQ ID NO 4
<211> LENGTH: 21
<212> TYPE: PRT
<213> ORGANISM: homo sapiens

<400> SEQUENCE: 4

Leu Pro Leu Leu Val Ala Gly Ala Val Leu Leu Leu Val Ile Leu Val
1               5                   10                  15

Leu Gly Val Met Val
            20

<210> SEQ ID NO 5
<211> LENGTH: 657
<212> TYPE: PRT
<213> ORGANISM: homo sapiens

<400> SEQUENCE: 5

Ala Arg Arg Lys Arg Glu His Ser Thr Leu Trp Phe Pro Glu Gly Phe
1               5                   10                  15

-continued

Ser Leu His Lys Asp Val Ala Ser Gly His Lys Gly Arg Glu Pro
        20                  25                  30

Val Gly Gln Asp Ala Leu Gly Met Lys Asn Met Ala Lys Gly Glu Ser
            35                  40                  45

Leu Met Gly Glu Val Ala Thr Asp Trp Met Asp Thr Glu Cys Pro Glu
 50                      55                  60

Ala Lys Arg Leu Lys Val Glu Glu Pro Gly Met Gly Ala Glu Glu Ala
 65              70                  75                      80

Val Asp Cys Arg Gln Trp Thr Gln His His Leu Val Ala Ala Asp Ile
                85                  90                  95

Arg Val Ala Pro Ala Met Ala Leu Thr Pro Gln Gly Asp Ala Asp
                100                 105                 110

Ala Asp Gly Met Asp Val Asn Val Arg Gly Pro Asp Gly Phe Thr Pro
            115                 120                 125

Leu Met Leu Ala Ser Phe Cys Gly Gly Ala Leu Glu Pro Met Pro Thr
130                     135                 140

Glu Glu Asp Glu Ala Asp Asp Thr Ser Ala Ser Ile Ile Ser Asp Leu
145                 150                 155                 160

Ile Cys Gln Gly Ala Gln Leu Gly Ala Arg Thr Asp Arg Thr Gly Glu
                165                 170                 175

Thr Ala Leu His Leu Ala Ala Arg Tyr Ala Arg Ala Asp Ala Ala Lys
            180                 185                 190

Arg Leu Leu Asp Ala Gly Ala Asp Thr Asn Ala Gln Asp His Ser Gly
        195                 200                 205

Arg Thr Pro Leu His Thr Ala Val Thr Ala Asp Ala Gln Gly Val Phe
210                 215                 220

Gln Ile Leu Ile Arg Asn Arg Ser Thr Asp Leu Asp Ala Arg Met Ala
225                 230                 235                 240

Asp Gly Ser Thr Ala Leu Ile Leu Ala Ala Arg Leu Ala Val Glu Gly
                245                 250                 255

Met Val Glu Glu Leu Ile Ala Ser His Ala Asp Val Asn Ala Val Asp
            260                 265                 270

Glu Leu Gly Lys Ser Ala Leu His Trp Ala Ala Ala Val Asn Asn Val
        275                 280                 285

Glu Ala Thr Leu Ala Leu Leu Lys Asn Gly Ala Asn Lys Asp Met Gln
290                 295                 300

Asp Ser Lys Glu Glu Thr Pro Leu Phe Leu Ala Ala Arg Glu Gly Ser
305                 310                 315                 320

Tyr Glu Ala Ala Lys Leu Leu Leu Asp His Phe Ala Asn Arg Glu Ile
                325                 330                 335

Thr Asp His Leu Asp Arg Leu Pro Arg Asp Val Ala Gln Glu Arg Leu
            340                 345                 350

His Gln Asp Ile Val Arg Leu Asp Gln Pro Ser Gly Pro Arg Ser
        355                 360                 365

Pro Pro Gly Pro His Gly Leu Gly Pro Leu Cys Pro Pro Gly Ala
    370                 375                 380

Phe Leu Pro Gly Leu Lys Ala Ala Gln Ser Gly Ser Lys Lys Ser Arg
385                 390                 395                 400

Arg Pro Pro Gly Lys Ala Gly Leu Gly Pro Gln Gly Pro Arg Gly Arg
                405                 410                 415

Gly Lys Lys Leu Thr Leu Ala Cys Pro Gly Pro Leu Ala Asp Ser Ser
            420                 425                 430

Val Thr Leu Ser Pro Val Asp Ser Leu Asp Ser Pro Arg Pro Phe Gly

```
                435                 440                 445
Gly Pro Pro Ala Ser Pro Gly Gly Phe Pro Leu Glu Gly Pro Tyr Ala
            450                 455                 460
Ala Ala Thr Ala Thr Ala Val Ser Leu Ala Gln Leu Gly Gly Pro Gly
465                 470                 475                 480
Arg Ala Gly Leu Gly Arg Gln Pro Pro Gly Cys Val Leu Ser Leu
                485                 490                 495
Gly Leu Leu Asn Pro Val Ala Val Pro Leu Asp Trp Ala Arg Leu Pro
            500                 505                 510
Pro Pro Ala Pro Pro Gly Pro Ser Phe Leu Leu Pro Leu Ala Pro Gly
            515                 520                 525
Pro Gln Leu Leu Asn Pro Gly Thr Pro Val Ser Pro Gln Glu Arg Pro
            530                 535                 540
Pro Pro Tyr Leu Ala Val Pro Gly His Gly Glu Glu Tyr Pro Ala Ala
545                 550                 555                 560
Gly Ala His Ser Ser Pro Pro Lys Ala Arg Phe Leu Arg Val Pro Ser
                565                 570                 575
Glu His Pro Tyr Leu Thr Pro Ser Pro Glu Ser Pro Glu His Trp Ala
            580                 585                 590
Ser Pro Ser Pro Pro Ser Leu Ser Asp Trp Ser Glu Ser Thr Pro Ser
        595                 600                 605
Pro Ala Thr Ala Thr Gly Ala Met Ala Thr Thr Thr Gly Ala Leu Pro
610                 615                 620
Ala Gln Pro Leu Pro Leu Ser Val Pro Ser Ser Leu Ala Gln Ala Gln
625                 630                 635                 640
Thr Gln Leu Gly Pro Gln Pro Glu Val Thr Pro Lys Arg Gln Val Leu
                645                 650                 655
Ala

<210> SEQ ID NO 6
<211> LENGTH: 1532
<212> TYPE: PRT
<213> ORGANISM: homo sapiens

<400> SEQUENCE: 6

Ala Pro Pro Cys Leu Asp Gly Ser Pro Cys Ala Asn Gly Gly Arg Cys
1               5                   10                  15
Thr Gln Leu Pro Ser Arg Glu Ala Ala Cys Leu Cys Pro Pro Gly Trp
            20                  25                  30
Val Gly Glu Arg Cys Gln Leu Glu Asp Pro Cys His Ser Gly Pro Cys
        35                  40                  45
Ala Gly Arg Gly Val Cys Gln Ser Ser Val Val Ala Gly Thr Ala Arg
    50                  55                  60
Phe Ser Cys Arg Cys Pro Arg Gly Phe Arg Gly Pro Asp Cys Ser Leu
65                  70                  75                  80
Pro Asp Pro Cys Leu Ser Ser Pro Cys Ala His Gly Ala Arg Cys Ser
                85                  90                  95
Val Gly Pro Asp Gly Arg Phe Leu Cys Ser Cys Pro Pro Gly Tyr Gln
            100                 105                 110
Gly Arg Ser Cys Arg Ser Asp Val Asp Glu Cys Arg Val Gly Glu Pro
        115                 120                 125
Cys Arg His Gly Gly Thr Cys Leu Asn Thr Pro Gly Ser Phe Arg Cys
    130                 135                 140
Gln Cys Pro Ala Gly Tyr Thr Gly Pro Leu Cys Glu Asn Pro Ala Val
```

```
            145                 150                 155                 160
        Pro Cys Ala Pro Ser Pro Cys Arg Asn Gly Gly Thr Cys Arg Gln Ser
                        165                 170                 175
        Gly Asp Leu Thr Tyr Asp Cys Ala Cys Leu Pro Gly Phe Glu Gly Gln
                        180                 185                 190
        Asn Cys Glu Val Asn Val Asp Cys Pro Gly His Arg Cys Leu Asn
                        195                 200                 205
        Gly Gly Thr Cys Val Asp Gly Val Asn Thr Tyr Asn Cys Gln Cys Pro
            210                 215                 220
        Pro Glu Trp Thr Gly Gln Phe Cys Thr Glu Asp Val Asp Glu Cys Gln
        225                 230                 235                 240
        Leu Gln Pro Asn Ala Cys His Asn Gly Gly Thr Cys Phe Asn Thr Leu
                        245                 250                 255
        Gly Gly His Ser Cys Val Cys Val Asn Gly Trp Thr Gly Glu Ser Cys
                        260                 265                 270
        Ser Gln Asn Ile Asp Asp Cys Ala Thr Ala Val Cys Phe His Gly Ala
                        275                 280                 285
        Thr Cys His Asp Arg Val Ala Ser Phe Tyr Cys Ala Cys Pro Met Gly
                        290                 295                 300
        Lys Thr Gly Leu Leu Cys His Leu Asp Asp Ala Cys Val Ser Asn Pro
        305                 310                 315                 320
        Cys His Glu Asp Ala Ile Cys Asp Thr Asn Pro Val Asn Gly Arg Ala
                        325                 330                 335
        Ile Cys Thr Cys Pro Pro Gly Phe Thr Gly Ala Cys Asp Gln Asp
                        340                 345                 350
        Val Asp Glu Cys Ser Ile Gly Ala Asn Pro Cys Glu His Leu Gly Arg
                        355                 360                 365
        Cys Val Asn Thr Gln Gly Ser Phe Leu Cys Gln Cys Gly Arg Gly Tyr
                        370                 375                 380
        Thr Gly Pro Arg Cys Glu Thr Asp Val Asn Glu Cys Leu Ser Gly Pro
        385                 390                 395                 400
        Cys Arg Asn Gln Ala Thr Cys Leu Asp Arg Ile Gly Gln Phe Thr Cys
                        405                 410                 415
        Ile Cys Met Ala Gly Phe Thr Gly Thr Tyr Cys Glu Val Asp Ile Asp
                        420                 425                 430
        Glu Cys Gln Ser Ser Pro Cys Val Asn Gly Gly Val Cys Lys Asp Arg
                        435                 440                 445
        Val Asn Gly Phe Ser Cys Thr Cys Pro Ser Gly Phe Ser Gly Ser Thr
            450                 455                 460
        Cys Gln Leu Asp Val Asp Glu Cys Ala Ser Thr Pro Cys Arg Asn Gly
        465                 470                 475                 480
        Ala Lys Cys Val Asp Gln Pro Asp Gly Tyr Glu Cys Arg Cys Ala Glu
                        485                 490                 495
        Gly Phe Glu Gly Thr Leu Cys Asp Arg Asn Val Asp Asp Cys Ser Pro
                        500                 505                 510
        Asp Pro Cys His His Gly Arg Cys Val Asp Gly Ile Ala Ser Phe Ser
                        515                 520                 525
        Cys Ala Cys Ala Pro Gly Tyr Thr Gly Thr Arg Cys Glu Ser Gln Val
                        530                 535                 540
        Asp Glu Cys Arg Ser Gln Pro Cys Arg His Gly Gly Lys Cys Leu Asp
        545                 550                 555                 560
        Leu Val Asp Lys Tyr Leu Cys Arg Cys Pro Ser Gly Thr Gly Val
                        565                 570                 575
```

```
Asn Cys Glu Val Asn Ile Asp Asp Cys Ala Ser Asn Pro Cys Thr Phe
            580                 585                 590

Gly Val Cys Arg Asp Gly Ile Asn Arg Tyr Asp Cys Val Cys Gln Pro
        595                 600                 605

Gly Phe Thr Gly Pro Leu Cys Asn Val Glu Ile Asn Glu Cys Ala Ser
610                 615                 620

Ser Pro Cys Gly Glu Gly Gly Ser Cys Val Asp Gly Glu Asn Gly Phe
625                 630                 635                 640

Arg Cys Leu Cys Pro Pro Gly Ser Leu Pro Pro Leu Cys Leu Pro Pro
                645                 650                 655

Ser His Pro Cys Ala His Glu Pro Cys Ser His Gly Ile Cys Tyr Asp
            660                 665                 670

Ala Pro Gly Gly Phe Arg Cys Val Cys Glu Pro Gly Trp Ser Gly Pro
        675                 680                 685

Arg Cys Ser Gln Ser Leu Ala Arg Asp Ala Cys Glu Ser Gln Pro Cys
690                 695                 700

Arg Ala Gly Gly Thr Cys Ser Ser Asp Gly Met Gly Phe His Cys Thr
705                 710                 715                 720

Cys Pro Pro Gly Val Gln Gly Arg Gln Cys Glu Leu Leu Ser Pro Cys
                725                 730                 735

Thr Pro Asn Pro Cys Glu His Gly Gly Arg Cys Glu Ser Ala Pro Gly
            740                 745                 750

Gln Leu Pro Val Cys Ser Cys Pro Gln Gly Trp Gln Gly Pro Arg Cys
        755                 760                 765

Gln Gln Asp Val Asp Glu Cys Ala Gly Pro Ala Pro Cys Gly Pro His
770                 775                 780

Gly Ile Cys Thr Asn Leu Ala Gly Ser Phe Ser Cys Thr Cys His Gly
785                 790                 795                 800

Gly Tyr Thr Gly Pro Ser Cys Asp Gln Asp Ile Asn Asp Cys Asp Pro
                805                 810                 815

Asn Pro Cys Leu Asn Gly Gly Ser Cys Gln Asp Gly Val Gly Ser Phe
            820                 825                 830

Ser Cys Ser Cys Leu Pro Gly Phe Ala Gly Pro Arg Cys Ala Arg Asp
        835                 840                 845

Val Asp Glu Cys Leu Ser Asn Pro Cys Gly Pro Gly Thr Cys Thr Asp
850                 855                 860

His Val Ala Ser Phe Thr Cys Thr Cys Pro Pro Gly Tyr Gly Gly Phe
865                 870                 875                 880

His Cys Glu Gln Asp Leu Pro Asp Cys Ser Pro Ser Ser Cys Phe Asn
                885                 890                 895

Gly Gly Thr Cys Val Asp Gly Val Asn Ser Phe Ser Cys Leu Cys Arg
            900                 905                 910

Pro Gly Tyr Thr Gly Ala His Cys Gln His Glu Ala Asp Pro Cys Leu
        915                 920                 925

Ser Arg Pro Cys Leu His Gly Gly Val Cys Ser Ala Ala His Pro Gly
930                 935                 940

Phe Arg Cys Thr Cys Leu Glu Ser Phe Thr Gly Pro Gln Cys Gln Thr
945                 950                 955                 960

Leu Val Asp Trp Cys Ser Arg Gln Pro Cys Gln Asn Gly Gly Arg Cys
                965                 970                 975

Val Gln Thr Gly Ala Tyr Cys Leu Cys Pro Pro Gly Trp Ser Gly Arg
            980                 985                 990
```

```
Leu Cys Asp Ile Arg Ser Leu Pro Cys Arg Glu Ala Ala Ala Gln Ile
            995                 1000                1005

Gly Val Arg Leu Glu Gln Leu Cys Gln Ala Gly Gly Gln Cys Val
    1010                1015                1020

Asp Glu Asp Ser Ser His Tyr Cys Val Cys Pro Glu Gly Arg Thr
    1025                1030                1035

Gly Ser His Cys Glu Gln Glu Val Asp Pro Cys Leu Ala Gln Pro
    1040                1045                1050

Cys Gln His Gly Gly Thr Cys Arg Gly Tyr Met Gly Gly Tyr Met
    1055                1060                1065

Cys Glu Cys Leu Pro Gly Tyr Asn Gly Asp Asn Cys Glu Asp Asp
    1070                1075                1080

Val Asp Glu Cys Ala Ser Gln Pro Cys Gln His Gly Gly Ser Cys
    1085                1090                1095

Ile Asp Leu Val Ala Arg Tyr Leu Cys Ser Cys Pro Pro Gly Thr
    1100                1105                1110

Leu Gly Val Leu Cys Glu Ile Asn Glu Asp Asp Cys Gly Pro Gly
    1115                1120                1125

Pro Pro Leu Asp Ser Gly Pro Arg Cys Leu His Asn Gly Thr Cys
    1130                1135                1140

Val Asp Leu Val Gly Gly Phe Arg Cys Thr Cys Pro Pro Gly Tyr
    1145                1150                1155

Thr Gly Leu Arg Cys Glu Ala Asp Ile Asn Glu Cys Arg Ser Gly
    1160                1165                1170

Ala Cys His Ala Ala His Thr Arg Asp Cys Leu Gln Asp Pro Gly
    1175                1180                1185

Gly Gly Phe Arg Cys Leu Cys His Ala Gly Phe Ser Gly Pro Arg
    1190                1195                1200

Cys Gln Thr Val Leu Ser Pro Cys Glu Ser Gln Pro Cys Gln His
    1205                1210                1215

Gly Gly Gln Cys Arg Pro Ser Pro Gly Pro Gly Gly Gly Leu Thr
    1220                1225                1230

Phe Thr Cys His Cys Ala Gln Pro Phe Trp Gly Pro Arg Cys Glu
    1235                1240                1245

Arg Val Ala Arg Ser Cys Arg Glu Leu Gln Cys Pro Val Gly Val
    1250                1255                1260

Pro Cys Gln Gln Thr Pro Arg Gly Pro Arg Cys Ala Cys Pro Pro
    1265                1270                1275

Gly Leu Ser Gly Pro Ser Cys Arg Ser Phe Pro Gly Ser Pro Pro
    1280                1285                1290

Gly Ala Ser Asn Ala Ser Cys Ala Ala Ala Pro Cys Leu His Gly
    1295                1300                1305

Gly Ser Cys Arg Pro Ala Pro Leu Ala Pro Phe Phe Arg Cys Ala
    1310                1315                1320

Cys Ala Gln Gly Trp Thr Gly Pro Arg Cys Glu Ala Pro Ala Ala
    1325                1330                1335

Ala Pro Glu Val Ser Glu Glu Pro Arg Cys Pro Arg Ala Ala Cys
    1340                1345                1350

Gln Ala Lys Arg Gly Asp Gln Arg Cys Asp Arg Glu Cys Asn Ser
    1355                1360                1365

Pro Gly Cys Gly Trp Asp Gly Gly Asp Cys Ser Leu Ser Val Gly
    1370                1375                1380

Asp Pro Trp Arg Gln Cys Glu Ala Leu Gln Cys Trp Arg Leu Phe
```

```
                    1385                1390                1395
Asn  Asn  Ser  Arg  Cys  Asp  Pro  Ala  Cys  Ser  Ser  Pro  Ala  Cys  Leu
               1400                1405                1410

Tyr  Asp  Asn  Phe  Asp  Cys  His  Ala  Gly  Gly  Arg  Glu  Arg  Thr  Cys
     1415                1420                1425

Asn  Pro  Val  Tyr  Glu  Lys  Tyr  Cys  Ala  Asp  His  Phe  Ala  Asp  Gly
     1430                1435                1440

Arg  Cys  Asp  Gln  Gly  Cys  Asn  Thr  Glu  Glu  Cys  Gly  Trp  Asp  Gly
     1445                1450                1455

Leu  Asp  Cys  Ala  Ser  Glu  Val  Pro  Ala  Leu  Leu  Ala  Arg  Gly  Val
     1460                1465                1470

Leu  Val  Leu  Thr  Val  Leu  Leu  Pro  Pro  Glu  Glu  Leu  Leu  Arg  Ser
     1475                1480                1485

Ser  Ala  Asp  Phe  Leu  Gln  Arg  Leu  Ser  Ala  Ile  Leu  Arg  Thr  Ser
     1490                1495                1500

Leu  Arg  Phe  Arg  Leu  Asp  Ala  His  Gly  Gln  Ala  Met  Val  Phe  Pro
     1505                1510                1515

Tyr  His  Arg  Pro  Ser  Pro  Gly  Ser  Glu  Pro  Arg  Ala  Arg  Arg
     1520                1525                1530

<210> SEQ ID NO 7
<211> LENGTH: 190
<212> TYPE: PRT
<213> ORGANISM: homo sapiens

<400> SEQUENCE: 7

Glu  Ile  Asn  Glu  Cys  Ala  Ser  Ser  Pro  Cys  Gly  Glu  Gly  Gly  Ser  Cys
1                   5                   10                  15

Val  Asp  Gly  Glu  Asn  Gly  Phe  Arg  Cys  Leu  Cys  Pro  Pro  Gly  Ser  Leu
               20                  25                  30

Pro  Pro  Leu  Cys  Leu  Pro  Pro  Ser  His  Pro  Cys  Ala  His  Glu  Pro  Cys
          35                  40                  45

Ser  His  Gly  Ile  Cys  Tyr  Asp  Ala  Pro  Gly  Gly  Phe  Arg  Cys  Val  Cys
     50                  55                  60

Glu  Pro  Gly  Trp  Ser  Gly  Pro  Arg  Cys  Ser  Gln  Ser  Leu  Ala  Arg  Asp
65                  70                  75                          80

Ala  Cys  Glu  Ser  Gln  Pro  Cys  Arg  Ala  Gly  Gly  Thr  Cys  Ser  Ser  Asp
               85                  90                  95

Gly  Met  Gly  Phe  His  Cys  Thr  Cys  Pro  Pro  Gly  Val  Gln  Gly  Arg  Gln
          100                 105                 110

Cys  Glu  Leu  Leu  Ser  Pro  Cys  Thr  Pro  Asn  Pro  Cys  Glu  His  Gly  Gly
     115                 120                 125

Arg  Cys  Glu  Ser  Ala  Pro  Gly  Gln  Leu  Pro  Val  Cys  Ser  Cys  Pro  Gln
130                 135                 140

Gly  Trp  Gln  Gly  Pro  Arg  Cys  Gln  Gln  Asp  Val  Asp  Glu  Cys  Ala  Gly
145                 150                 155                         160

Pro  Ala  Pro  Cys  Gly  Pro  His  Gly  Ile  Cys  Thr  Asn  Leu  Ala  Gly  Ser
               165                 170                 175

Phe  Ser  Cys  Thr  Cys  His  Gly  Gly  Tyr  Thr  Gly  Pro  Ser  Cys
          180                 185                 190

<210> SEQ ID NO 8
<211> LENGTH: 8
<212> TYPE: PRT
<213> ORGANISM: artificial
<220> FEATURE:
```

<223> OTHER INFORMATION: Antibody CDR region

<400> SEQUENCE: 8

Gly Tyr Thr Phe Thr Ser Tyr Trp
1               5

<210> SEQ ID NO 9
<211> LENGTH: 8
<212> TYPE: PRT
<213> ORGANISM: artificial
<220> FEATURE:
<223> OTHER INFORMATION: Antibody CDR region

<400> SEQUENCE: 9

Ile Tyr Pro Gly Asn Gly Asp Thr
1               5

<210> SEQ ID NO 10
<211> LENGTH: 14
<212> TYPE: PRT
<213> ORGANISM: artificial
<220> FEATURE:
<223> OTHER INFORMATION: Antibody CRD region

<400> SEQUENCE: 10

Thr Arg Asp Tyr Gly Ser Ser Tyr Asp Tyr Val Met Asp Tyr
1               5                   10

<210> SEQ ID NO 11
<211> LENGTH: 121
<212> TYPE: PRT
<213> ORGANISM: artificial
<220> FEATURE:
<223> OTHER INFORMATION: Antibody VH region

<400> SEQUENCE: 11

Glu Ile Gln Leu Gln Gln Ser Gly Thr Val Leu Ala Arg Pro Gly Ala
1               5                   10                  15

Ser Val Lys Met Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Ala Ile Tyr Pro Gly Asn Gly Asp Thr Ser Tyr Asn Arg Lys Phe
    50                  55                  60

Asn Gly Lys Ala Lys Leu Thr Ala Val Thr Ser Thr Ser Thr Ala Tyr
65                  70                  75                  80

Met Glu Phe Ser Ser Leu Thr Asn Glu Asp Ser Ala Val Tyr Phe Cys
                85                  90                  95

Thr Arg Asp Tyr Gly Ser Ser Tyr Asp Tyr Val Met Asp Tyr Trp Gly
            100                 105                 110

Gln Gly Thr Ser Val Thr Val Ser Ser
        115                 120

<210> SEQ ID NO 12
<211> LENGTH: 5
<212> TYPE: PRT
<213> ORGANISM: artificial
<220> FEATURE:
<223> OTHER INFORMATION: Antibody CDR region

<400> SEQUENCE: 12

Asp Ile Gly Ser Ser
1               5

```
<210> SEQ ID NO 13
<211> LENGTH: 3
<212> TYPE: PRT
<213> ORGANISM: artificial
<220> FEATURE:
<223> OTHER INFORMATION: Antibody CDR region

<400> SEQUENCE: 13

Ala Thr Ser
1

<210> SEQ ID NO 14
<211> LENGTH: 9
<212> TYPE: PRT
<213> ORGANISM: artificial
<220> FEATURE:
<223> OTHER INFORMATION: Antibody CDR region

<400> SEQUENCE: 14

Leu Gln Tyr Ile Ser Ser Pro Leu Thr
1               5

<210> SEQ ID NO 15
<211> LENGTH: 107
<212> TYPE: PRT
<213> ORGANISM: artificial
<220> FEATURE:
<223> OTHER INFORMATION: Antibody VL region

<400> SEQUENCE: 15

Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Asp Ile Gly Ser Ser
            20                  25                  30

Leu Asn Trp Leu Gln Gln Glu Pro Asp Gly Thr Ile Lys Arg Leu Ile
        35                  40                  45

Tyr Ala Thr Ser Ser Leu Asp Ser Gly Val Pro Lys Arg Phe Ser Gly
    50                  55                  60

Ser Arg Ser Gly Ser Asp Tyr Ser Leu Thr Ile Ser Arg Leu Glu Ser
65                  70                  75                  80

Glu Asp Phe Val Asp Tyr Tyr Cys Leu Gln Tyr Ile Ser Ser Pro Leu
                85                  90                  95

Thr Phe Gly Ala Gly Thr Lys Leu Glu Leu Lys
            100                 105
```